(12) United States Patent
Jonczyk et al.

(10) Patent No.: US 6,566,491 B2
(45) Date of Patent: May 20, 2003

(54) CYCLOPEPTIDE DERIVATIVES

(75) Inventors: Alfred Jonczyk, Darmstadt (DE); Simon Lawrence Goodman, Darmstadt (DE); Beate Diefenbach, Darmstadt (DE); Arne Sutter, Darmstadt (DE); Horst Kessler, Garching (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/051,603

(22) PCT Filed: Oct. 4, 1996

(86) PCT No.: PCT/EP96/04462

§ 371 (c)(1), (2), (4) Date: Aug. 18, 1998

(87) PCT Pub. No.: WO97/14716

PCT Pub. Date: Apr. 24, 1997

(65) Prior Publication Data

US 2002/0032306 A1 Mar. 14, 2002

(30) Foreign Application Priority Data

Oct. 18, 1995 (DE) .......................................... 195 38 741

(51) Int. Cl.⁷ ............................................... A61K 38/12
(52) U.S. Cl. ............................... 530/317; 514/9; 514/11
(58) Field of Search ..................... 514/2, 9, 11; 530/317

(56) References Cited

U.S. PATENT DOCUMENTS 5,849,692 A * 12/1998 Jonczyk et al. ................ 514/11

OTHER PUBLICATIONS

Database CaPlus, DN 97:1969. Johnson et al. J. Biol. Chem., 257(10), 5632–6, May 1982.*

Database CaPlus DN 90:148010. Valet et al. J. Histochem. Cytochem. (1979), 27(1), 342–9, Jan. 1979.*

"Remington Pharmaceutical Science", part 8, Mack Publishing Co., Easton, PA, 1980.*

* cited by examiner

Primary Examiner—Michael Borin
(74) Attorney, Agent, or Firm—Millen, White, Zelano & Branigan, P.C.

(57) ABSTRACT

The invention relates to compounds of the formula (I) $R^1$—$Q^1$—X—$Q^2$—$R^2$, in which: $Q^1$, $Q^2$, each independent of one another, are missing or are —NH—$(CH_2)_n$—CO—; $R^1$, $R^2$, each independent of one another, are missing or are cyclo-(Arg-Gly-Asp-Z), wherein Z is missing in side chain of $Q^1$ or $Q^2$ of if $Q^1$ and/or $Q^2$ missing, is bound to X, at least one of the groups $R^1$ or $R^2$ always having to be included; X is —CO—$R^{18}$—CO—, and if $R^1$—$Q^1$— or $R^2$—$Q^2$— are missing is $R^{10}$, $R^{13}$, Het-CO or a flourescent pigment residue linked through a —CONH—, —COO—, NH—C(=S)—N—, —NH—C(=O)—NH—, —$SO_2$ NH—or —NHCO— bond; and Z, $R^{10}$, $R^{13}$, $R^{16}$, $R^{18}$, Het and n have the meaning given in claim 1. The invention also relates to the salts of said compounds. These compounds and their salts can be used as integrin inhibitors, in particular for the prevention and treatment of circulatory diseases, thrombosis, heart infarct, coronary heart diseases, arteriosclerosis, angiogenic diseases and in tumor therapy.

10 Claims, No Drawings

SEQUENCE LISTING

```
<160> NUMBER OF SEQ ID NOS: 214

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-Sal (epsilon amino group modified
      with salicyloyl)

<400> SEQUENCE: 1

Arg Gly Asp Xaa Xaa
  1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-PhEtCO (epsilon amino group modified with
      Ph-Et-CO)

<400> SEQUENCE: 2

Arg Gly Asp Xaa Xaa
  1               5

<210> SEQ ID NO 3
<211> LENGTH: 5
<212> TYPE: PRT
```

```
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-TCPP (epsilon amino group modified
      with 3,3,3-tris-(4-chlorophenyl)-propionyl)

<400> SEQUENCE: 3

Arg Gly Asp Xaa Xaa
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-TrtSEtCO (epsilon amino group modified
      with S-tritylmercaptopropionyl)

<400> SEQUENCE: 4

Arg Gly Asp Xaa Xaa
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-CBZ (epsilon amino group modified
      with benzyloxycarbonyl)

<400> SEQUENCE: 5

Arg Gly Asp Xaa Xaa
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
```

-continued

```
<222> LOCATION: (5)
<223> OTHER INFORMATION: Lys-N-eps-Oct (epsilon amino group modified
      with octanoyl)

<400> SEQUENCE: 6

Arg Gly Asp Xaa Xaa
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-Ac (epsilon amino group modified
      with acetyl)

<400> SEQUENCE: 7

Arg Gly Asp Xaa Xaa
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-FCA (epsilon amino group modified
      with fluoresceincarbonyl)

<400> SEQUENCE: 8

Arg Gly Asp Xaa Xaa
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:cyclopeptide
      derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-FTH (epsilon amino group modified
      with fluorescein-NH-C(=S)-)

<400> SEQUENCE: 9

Arg Gly Asp Xaa Xaa
 1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: N-Me-Lys (N-methyl-lysine)

<400> SEQUENCE: 10

Arg Gly Asp Xaa Xaa
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: NMe-Lys-N-FTH
      (N-methyl-lysine-N-epsilon-(fluorescein-NH-C(=S)-))

<400> SEQUENCE: 11

Arg Gly Asp Xaa Xaa
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: NMe-Lys-N-CBZ
      (N-methyl-lysine-N-epsilon-(benzyloxycarbonyl-))

<400> SEQUENCE: 12

Arg Gly Asp Xaa Xaa
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
```

```
<220> FEATURE:
<221> NAME/KEY: MOD_RES
<222> LOCATION: (5)
<223> OTHER INFORMATION: Lys-N-Boc-Aha (epsilon amino group modified
      with tert.-butyloxycarbonyl-amino-hexanoyl)

<400> SEQUENCE: 13

Arg Gly Asp Xaa Xaa
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-eps-Aha
      (epsilon amino group modified with aminohexanoyl)

<400> SEQUENCE: 14

Arg Gly Asp Xaa Xaa
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-FCA-Aha (epsilon amino group modified
      with fluoresceincarbonyl-amino-hexanoyl)

<400> SEQUENCE: 15

Arg Gly Asp Xaa Xaa
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-FTH-Aha (epsilon amino group modified
      with fluorescein-NH-C(=S)-amino-hexan)

<400> SEQUENCE: 16

Arg Gly Asp Xaa Xaa
 1               5
```

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-Ac-Aha (epsilon amino group modified
      with acetyl-aminohexanoyl)

<400> SEQUENCE: 17

Arg Gly Asp Xaa Xaa
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-BOC-Aha (epsilon amino group modified
      with tert.-butyloxycarbonyl-amino-hexanoyl)

<400> SEQUENCE: 18

Arg Gly Asp Xaa Xaa Gly
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-Aha (epsilon amino group modified with
      aminohexanoyl)

<400> SEQUENCE: 19

Arg Gly Asp Xaa Xaa Gly
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:

```
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-PhEtCOAha (epsilon amino group modified
      with phenylpropionyl-amino-hexanoyl)

<400> SEQUENCE: 20

Arg Gly Asp Xaa Xaa Gly
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-Oct-Aha (epsilon amino group modified
      with octanoyl-amino-hexanoyl)

<400> SEQUENCE: 21

Arg Gly Asp Xaa Xaa Gly
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-FCA-Aha (epsilon amino group modified
      with fluoresceincarbonyl-amino-hexanoyl)

<400> SEQUENCE: 22

Arg Gly Asp Xaa Xaa Gly
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-FTH-Aha (epsilon amino group modified
      with fluorescein-NH-C(=S)-amino-hexan...)

<400> SEQUENCE: 23
```

Arg Gly Asp Xaa Xaa Gly
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (6)
<223> OTHER INFORMATION: Lys-N-BOC-Aha (epsilon amino group modified
      with tert.-butyloxycarbonyl-amino-hexanoyl)

<400> SEQUENCE: 24

Arg Gly Asp Xaa Val Xaa
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (6)
<223> OTHER INFORMATION: Lys-N-Aha (epsilon amino group modified with
      aminohexanoyl)

<400> SEQUENCE: 25

Arg Gly Asp Xaa Val Xaa
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (6)
<223> OTHER INFORMATION: Lys-N-PhEtCOAha (epsilon amino group modified
      with phenylpropionylamino-hexanoyl)

<400> SEQUENCE: 26

Arg Gly Asp Xaa Val Xaa
 1               5

<210> SEQ ID NO 27
<211> LENGTH: 5
<212> TYPE: PRT
<213> ORGANISM: Artificial Sequence
<220> FEATURE:

```
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Lys-N-BOC-Aha (epsilon amino group modified
      with tert.-butyloxycarbonyl-amino-hexanoyl)

<400> SEQUENCE: 27

Arg Gly Asp Xaa Xaa
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Lys-N-BOC-Aha (epsilon amino group modified
      with tert.-butyloxycarbonyl-aminohexa)

<400> SEQUENCE: 28

Arg Gly Asp Xaa Xaa
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Lys-N-BOC-Aha (epsilon amino group of D-Lys
      modified with tert.-butyloxycarbonyl-aminohexanoyl)

<400> SEQUENCE: 29

Arg Gly Asp Xaa Xaa
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Cys-S-BOC-Aha (thiol group modified with
``` tert.-butyloxycarbonyl-amino-hexanoyl)

<400> SEQUENCE: 30

Arg Gly Asp Xaa Xaa
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dbu-N-BOC-Aha (gamma amino group of Dbu
      (2,4-diaminobutyric acid) modified with ter.-butyloxycarbonyl-
      aminohexanoyl)

<400> SEQUENCE: 31

Arg Gly Asp Xaa Xaa
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Cys-S-BOC-Aha (thiol group of D-Cys modified
      with tert.-butyloxycarbonyl-amino-hexanoyl)

<400> SEQUENCE: 32

Arg Gly Asp Xaa Xaa
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Cys-S-BOC-Aha (thiol group of D-Cys modified
      with tert.-butyloxycarbonyl-amino-hexanoyl)

<400> SEQUENCE: 33

Arg Gly Asp Xaa Xaa
 1               5

<210> SEQ ID NO 34

```
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-BOC-Aha (epsilon amino group of D-Lys
      modified with tert.-butyloxycarbonyl-aminohexanoyl)

<400> SEQUENCE: 34

Arg Gly Asp Phe Xaa
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-BOC-Aha (epsilon amino group of
      D-lysine modified with tert.-butyloxy-carbonyl-aminohexanoyl)

<400> SEQUENCE: 35

Arg Gly Asp Trp Xaa
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-BOC-Aha (epsilon amino group of
      D-Lys modified with tert.-butyloxy-carbonyl-aminohexanoyl)

<400> SEQUENCE: 36

Arg Gly Asp Tyr Xaa
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-BOC-Aha (thiol group of D-Cys modified
      with tert.-butyloxycarbonyl-amino-hexanoyl)

<400> SEQUENCE: 37

Arg Gly Asp Phe Xaa
 1               5

<210> SEQ ID NO 38
<211> LENGTH: 5
<212> TYPE: PRT
<213> ORGANISM: Artificial Sequence
```

```
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: Dbu-N-BOC-Aha (gamma amino group of Dbu
      modified with tert.-butyloxycarbonyl-aminohexanoyl)

<400> SEQUENCE: 38

Arg Gly Asp Phe Xaa
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-BOC-Aha (thiol group of D-Cys modified
      with tert.-butyloxycarbonyl-aminohexanoyl)

<400> SEQUENCE: 39

Arg Gly Asp Trp Xaa
 1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-BOC-Aha (thiol group of D-Cys modified
      with tert.-butyloxycarbonyl-aminohexanoyl)

<400> SEQUENCE: 40

Arg Gly Asp Tyr Xaa
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Orn-N-BOC-Aha (delta amino group of Orn
      modified with tert.-butyloxycarbonyl-aminohexanoyl)

<400> SEQUENCE: 41

Arg Gly Asp Xaa Xaa
 1               5

<210> SEQ ID NO 42
<211> LENGTH: 5
<212> TYPE: PRT
```

```
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Orn-N-BOC-Aha (delta amino group of Orn
      modified with tert.-butyloxycarbonyl-aminohexanoyl)

<400> SEQUENCE: 42

Arg Gly Asp Xaa Xaa
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Orn-N-BOC-Aha (delta amino group of Orn
      modified with tert.-butyloxycarbonyl-aminohexanoyl)

<400> SEQUENCE: 43

Arg Gly Asp Xaa Xaa
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Orn-N-BOC-Aha (delta amino group of D-Orn
      modified with tert.-butyloxycarbonyl-aminohexanoyl)

<400> SEQUENCE: 44

Arg Gly Asp Xaa Xaa
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
```

```
<222> LOCATION: (5)
<223> OTHER INFORMATION: D-Orn-N-BOC-Aha (delta amino group of D-Orn
      modified with tert.-butyloxycarbonyl-aminohexanoyl)

<400> SEQUENCE: 45

Arg Gly Asp Xaa Xaa
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Orn-N-BOC-Aha (delta amino group of D-Orn
      modified with tert.-butyloxycarbonyl-aminohexanoyl)

<400> SEQUENCE: 46

Arg Gly Asp Xaa Xaa
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dbu-N-BOC-Aha (gamma amino group of Dbu
      modified with tert.-butyloxycarbonyl-aminohexanoyl)

<400> SEQUENCE: 47

Arg Gly Asp Xaa Xaa
 1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dbu-N-BOC-Aha (gamma amino group of Dbu
      modified with tert.-butyloxycarbonyl-aminohexanoyl)

<400> SEQUENCE: 48

Arg Gly Asp Xaa Xaa
 1               5
```

```
<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dpr-N-BOC-Aha (beta amino group of Dpr modified
      with tert.-butyloxycarbonyl-aminohexanoyl)

<400> SEQUENCE: 49

Arg Gly Asp Xaa Xaa
 1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dpr-N-BOC-Aha (beta amino group of Dpr modified
      with tert.-butyloxycarbonyl-aminohexanoyl)

<400> SEQUENCE: 50

Arg Gly Asp Xaa Xaa
 1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dpr-N-BOC-Aha (beta amino group of Dpr modified
      with tert.-butyloxycarbonyl-aminohexanoyl)

<400> SEQUENCE: 51

Arg Gly Asp Xaa Xaa
 1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
```

```
<223> OTHER INFORMATION: D-Trp
<220> FEATURE:
<221> NAME/KEY: MOD_RES
<222> LOCATION: (5)
<223> OTHER INFORMATION: D-Dpr-N-BOC-Aha (beta amino group of D-Dpr
      modified with tert.-butyloxycarbonyl-aminohexanoyl)

<400> SEQUENCE: 52

Arg Gly Asp Xaa Xaa
 1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Dpr-N-BOC-Aha (beta amino group of D-Dpr
      modified with tert.-butyloxycarbonyl-aminohexanoyl)

<400> SEQUENCE: 53

Arg Gly Asp Xaa Xaa
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Dpr-N-BOC-Aha (beta amino group of D-Dpr
      modified with tert.-butyloxycarbonyl-aminohexanoyl)

<400> SEQUENCE: 54

Arg Gly Asp Xaa Xaa
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Lys-N-Aha (epsilon amino group of Lys modified
      with aminohexanoyl)

<400> SEQUENCE: 55

Arg Gly Asp Xaa Xaa
```

```
<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Lys-N-Aha (epsilon amino group of Lys modified
      with aminohexanoyl)

<400> SEQUENCE: 56

Arg Gly Asp Xaa Xaa
 1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Lys-N-Aha (epsilon amino group of D-Lys
      modified with aminohexanoyl)

<400> SEQUENCE: 57

Arg Gly Asp Xaa Xaa
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Cys-S-Aha (thiol group of Cys modified with
      aminohexanoyl)

<400> SEQUENCE: 58

Arg Gly Asp Xaa Xaa
 1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
```

```
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dbu-N-Aha (gamma amino group of Dbu modified
      with aminohexanoyl)

<400> SEQUENCE: 59

Arg Gly Asp Xaa Xaa
  1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Cys-S-Aha (thiol group of D-Cys modified
      with aminohexanoyl)

<400> SEQUENCE: 60

Arg Gly Asp Xaa Xaa
  1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Cys-S-Aha (thiol group of D-Cys modified
      with aminohexanoyl)

<400> SEQUENCE: 61

Arg Gly Asp Xaa Xaa
  1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-Aha (epsilon amino group of D-Lys
      modified with aminohexanoyl)

<400> SEQUENCE: 62

Arg Gly Asp Phe Xaa
  1               5
```

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-Aha (epsilon amino group of D-Lys
      modified with aminohexanoyl)

<400> SEQUENCE: 63

Arg Gly Asp Trp Xaa
 1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-Aha (epsilon aminogroup of D-Lys
      modified with aminohexanoyl)

<400> SEQUENCE: 64

Arg Gly Asp Tyr Xaa
 1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-Aha (thiol group of D-Cys modified
      with aminohexanoyl)

<400> SEQUENCE: 65

Arg Gly Asp Phe Xaa
 1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: Dbu-N-Aha (gamma amino group of Dbu modified
      with aminohexanoyl)

<400> SEQUENCE: 66

Arg Gly Asp Phe Xaa
 1               5

<210> SEQ ID NO 67

```
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-Aha (thiol group of D-Cys modified
      with aminohexanoyl)

<400> SEQUENCE: 67

Arg Gly Asp Trp Xaa
 1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-Aha (thiol group of D-Cys modified
      with aminohexanoyl)

<400> SEQUENCE: 68

Arg Gly Asp Tyr Xaa
 1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Orn-N-Aha (delta amino group of Orn modified
      with aminohexanoyl)

<400> SEQUENCE: 69

Arg Gly Asp Xaa Xaa
 1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Orn-N-Aha delta amino group of Orn modified
      with aminohexanoyl)

<400> SEQUENCE: 70
```

Arg Gly Asp Xaa Xaa
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Orn-N-Aha (delta amino group of Orn modified
      with aminohexanoyl)

<400> SEQUENCE: 71

Arg Gly Asp Xaa Xaa
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Orn-N-Aha (delta amino group of D-Orn
      modified with aminohexanoyl)

<400> SEQUENCE: 72

Arg Gly Asp Xaa Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Orn-N-Aha (delta amino group of D-Orn
      modified with aminohexanoyl)

<400> SEQUENCE: 73

Arg Gly Asp Xaa Xaa
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence:

```
            cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Orn-N-Aha (delta amino group of D-Orn
      modified with aminohexanoyl)

<400> SEQUENCE: 74

Arg Gly Asp Xaa Xaa
 1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dbu-N-Aha (gamma amino group of Dbu modified
      with aminohexanoyl)

<400> SEQUENCE: 75

Arg Gly Asp Xaa Xaa
 1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dbu-N-Aha (gamma amino group of Dbu modified
      with aminohexanoyl)

<400> SEQUENCE: 76

Arg Gly Asp Xaa Xaa
 1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dpr-N-Aha (beta amino group of Dpr modified
      with aminohexanoyl)
```

<400> SEQUENCE: 77

Arg Gly Asp Xaa Xaa
 1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dpr-N-Aha (beta amino group of Dpr modified
      with aminohexanoyl)

<400> SEQUENCE: 78

Arg Gly Asp Xaa Xaa
 1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dpr-N-Aha (beta amino group of Dpr modifies
      with aminohexanoyl)

<400> SEQUENCE: 79

Arg Gly Asp Xaa Xaa
 1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Dpr-N-Aha (beta amino group of D-Dpr modified
      with aminohexanoyl)

<400> SEQUENCE: 80

Arg Gly Asp Xaa Xaa
 1               5

<210> SEQ ID NO 81
<211> LENGTH: 5
<212> TYPE: PRT

```
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Dpr-N-Aha (beta amino group of D-Dpr modified
      with aminohexanoyl)

<400> SEQUENCE: 81

Arg Gly Asp Xaa Xaa
 1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Dpr-N-Aha (beta amino group of D-Dpr modified
      with aminohexanoyl)

<400> SEQUENCE: 82

Arg Gly Asp Xaa Xaa
 1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Lys-N-Oct-Aha (epsilon amino group of Lys
      modified with octanoyl-amino-hexanoyl)

<400> SEQUENCE: 83

Arg Gly Asp Xaa Xaa
 1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
```

```
<222> LOCATION: (5)
<223> OTHER INFORMATION: Lys-N-Oct-Aha (epsilon amino group of Lys
      modified with octanoyl-amino-hexanoyl)

<400> SEQUENCE: 84

Arg Gly Asp Xaa Xaa
  1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Lys-N-Oct-Aha (epsilon amino group of D-Lys
      modified with octanoyl-amino-hexanoyl)

<400> SEQUENCE: 85

Arg Gly Asp Xaa Xaa
  1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Cys-S-Oct-Aha (thiol group of Cys modified with
      octanoyl-amino-hexanoyl)

<400> SEQUENCE: 86

Arg Gly Asp Xaa Xaa
  1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dbu-N-Oct-Aha (gamma amino group of Dbu modified with
      octanoyl-amino-hexanoyl)

<400> SEQUENCE: 87

Arg Gly Asp Xaa Xaa
  1               5
```

```
<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Cys-S-Oct-Aha (thiol group of D-Cys modified with
      octanoyl-amino-hexanoyl)

<400> SEQUENCE: 88

Arg Gly Asp Xaa Xaa
 1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Cys-S-Oct-Aha (thiol group of D-Cys modified with
      octanoyl-amino-hexanoyl)

<400> SEQUENCE: 89

Arg Gly Asp Xaa Xaa
 1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-Oct-Aha (epsilon amino group of D-Lys
      modified with octanoyl-amino-hexanoyl)

<400> SEQUENCE: 90

Arg Gly Asp Phe Xaa
 1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-Oct-Aha (epsilon amino group of D-Lys
      modified with octanoyl-amino-hexanoyl)

<400> SEQUENCE: 91
```

Arg Gly Asp Trp Xaa
  1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-Oct-Aha (epsilon amino group of D-Lys
      modified with octanoyl-amino-hexanoyl)

<400> SEQUENCE: 92

Arg Gly Asp Tyr Xaa
  1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-Oct-Aha (thiol group of D-Cys modified
      with octanoyl-amino-hexanoyl)

<400> SEQUENCE: 93

Arg Gly Asp Phe Xaa
  1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: Dbu-N-Oct-Aha (gamma amino group of Dbu
      modified with octanoyl-amino-hexanoyl)

<400> SEQUENCE: 94

Arg Gly Asp Phe Xaa
  1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-Oct-Aha (thiol group of D-Cys modified
      with octanoyl-amino-hexanoyl)

<400> SEQUENCE: 95

Arg Gly Asp Trp Xaa
  1               5

```
<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-Oct-Aha (thiol group of D-Cys modified
      with octanoyl-amino-hexanoyl)

<400> SEQUENCE: 96

Arg Gly Asp Tyr Xaa
 1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Orn-N-Oct-Aha (delta amino group of Orn
      modified with octanoyl-amino-hexanoyl)

<400> SEQUENCE: 97

Arg Gly Asp Xaa Xaa
 1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Orn-N-Oct-Aha (delta amino group of Orn
      modified with octanoyl-amino-hexanoyl)

<400> SEQUENCE: 98

Arg Gly Asp Xaa Xaa
 1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
```

```
<221> NAME/KEY: MOD_RES
<222> LOCATION: (5)
<223> OTHER INFORMATION: Orn-N-Oct-Aha (delta amino group of Orn
      modified with octanoyl-amino-hexanoyl)

<400> SEQUENCE: 99

Arg Gly Asp Xaa Xaa
 1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Orn-N-Oct-Aha (delta amino group of D-Orn
      modified with octanoyl-amino-hexanoyl)

<400> SEQUENCE: 100

Arg Gly Asp Xaa Xaa
 1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Orn-N-Oct-Aha (delta amino group of D-Orn
      modified with octanoyl-amino-hexanyol)

<400> SEQUENCE: 101

Arg Gly Asp Xaa Xaa
 1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Orn-N-Oct-Aha (delta amino group of D-Orn
      modified with octanoyl-amino-hexanoyl)

<400> SEQUENCE: 102

Arg Gly Asp Xaa Xaa
 1               5
```

```
<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dbu-N-Oct-Aha (gamma amino group of Dbu
      modified with octanoyl-amino-hexanoyl)

<400> SEQUENCE: 103

Arg Gly Asp Xaa Xaa
 1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dbu-N-Oct-Aha (gamma amino group of Dbu
      modified with octanoyl-amino-hexanoyl)

<400> SEQUENCE: 104

Arg Gly Asp Xaa Xaa
 1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dpr-N-Oct-Aha (beta amino group of Dpr modified
      with octanoyl-amino-hexanoyl)

<400> SEQUENCE: 105

Arg Gly Asp Xaa Xaa
 1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
```

```
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dpr-N-Oct-Aha (beta amino group of Dpr modified
      with octanoyl-amino-hexanoyl)

<400> SEQUENCE: 106

Arg Gly Asp Xaa Xaa
 1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dpr-N-Oct-Aha (beta amino group of Dpr modified
      with octanoyl-amino-hexanoyl)

<400> SEQUENCE: 107

Arg Gly Asp Xaa Xaa
 1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Dpr-N-Oct-Aha (beta amino group of D-Dpr
      modified with octanoyl-amino-hexanoyl)

<400> SEQUENCE: 108

Arg Gly Asp Xaa Xaa
 1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Dpr-N-Oct-Aha (beta amino group of D-Dpr
      modified with octanoyl-amino-hexanoyl)

<400> SEQUENCE: 109
```

Arg Gly Asp Xaa Xaa
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Dpr-N-Oct-Aha (beta amino group of D-Dpr
      modified with octanoyl-amino-hexanoyl)

<400> SEQUENCE: 110

Arg Gly Asp Xaa Xaa
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Lys-N-FCA-Aha (epsilon amino group of Lys
      modified with fluoresceincarbonyl-amino-hexanoyl)

<400> SEQUENCE: 111

Arg Gly Asp Xaa Xaa
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Lys-N-FCA-Aha (epsilon amino group of Lys
      modified with fluoresceincarbonyl-amino-hexanoyl)

<400> SEQUENCE: 112

Arg Gly Asp Xaa Xaa
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence:

```
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Lys-N-FCA-Aha (epsilon amino group of D-Lys
      modified with fluoresceincarbonyl-amino-hexanoyl)

<400> SEQUENCE: 113

Arg Gly Asp Xaa Xaa
 1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Cys-S-FCA-Aha (thiol group of Cys modified with
      fluoresceincarbonyl-amino-hexanoyl)

<400> SEQUENCE: 114

Arg Gly Asp Xaa Xaa
 1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dbu-N-FCA-Aha (gamma amino group of Dbu
      modified with fluoresceincarbonyl-amino-hexanoyl)

<400> SEQUENCE: 115

Arg Gly Asp Xaa Xaa
 1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Cys-S-FCA-Aha (thiol group of D-Cys modified
      with fluoresceincarbonyl-amino-hexan...)
```

```
<400> SEQUENCE: 116

Arg Gly Asp Xaa Xaa
 1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Cys-S-FCA-Aha (thiol group of D-Cys
      modified with fluoresceincarbonyl-amino-hexan...)

<400> SEQUENCE: 117

Arg Gly Asp Xaa Xaa
 1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-FCA-Aha (epsilon amino group of D-Lys
      modified with fluoresceincarbonyl-amino-hexanoyl)

<400> SEQUENCE: 118

Arg Gly Asp Phe Xaa
 1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-FCA-Aha (epsilon amino group of D-Lys
      modified with fluoresceincarbonyl-aminohexanoyl)

<400> SEQUENCE: 119

Arg Gly Asp Trp Xaa
 1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-FCA-Aha (epsilon amino group of D-Lys
``` modified with fluoresceincarbonyl-aminohexanoyl)

<400> SEQUENCE: 120

Arg Gly Asp Tyr Xaa
1               5

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-FCA-Aha (thiol group of D-Cys modified
      with fluoresceincarbonyl-amino-hexan...)

<400> SEQUENCE: 121

Arg Gly Asp Phe Xaa
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: Dbu-N-FCA-Aha (gamma amino group of Dbu modified
      with fluoresceincarbonyl-amino-hexanoyl)

<400> SEQUENCE: 122

Arg Gly Asp Phe Xaa
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-FCA-Aha (thiol group of D-Cys modified
      with fluoresceincarbonyl-amino-hexan...)

<400> SEQUENCE: 123

Arg Gly Asp Trp Xaa
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-FCA-Aha (thiol group of D-Cys modified
      with fluoresceincarbonyl-amino-hexan...)

<400> SEQUENCE: 124

Arg Gly Asp Tyr Xaa
 1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Orn-N-FCA-Aha (delta amino group of Orn
      modified with fluoresceincarbonyl-aminohexanoyl)

<400> SEQUENCE: 125

Arg Gly Asp Xaa Xaa
 1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Orn-N-FCA-Aha (delta amino group of Orn
      modified with fluoresceincarbonyl-aminohexanoyl)

<400> SEQUENCE: 126

Arg Gly Asp Xaa Xaa
 1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Orn-N-FCA-Aha (delta amino group of Orn
      modified with fluoresceincarbonyl-amino-hexanoyl)

<400> SEQUENCE: 127

Arg Gly Asp Xaa Xaa
 1               5

<210> SEQ ID NO 128
<211> LENGTH: 5
<212> TYPE: PRT
<213> ORGANISM: Artificial Sequence
<220> FEATURE:

```
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Orn-N-FCA-Aha (delta amino group of D-Orn
      modified with fluoresceincarbonyl-aminohexanoyl)

<400> SEQUENCE: 128

Arg Gly Asp Xaa Xaa
 1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Orn-N-FCA-Aha (delta amino group of D-Orn
      modified with fluoresceincarbonyl-aminohexanoyl)

<400> SEQUENCE: 129

Arg Gly Asp Xaa Xaa
 1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Orn-N-FCA-Aha (delta amino group of D-Orn
      modified with fluoresceincarbonyl-aminohexanoyl)

<400> SEQUENCE: 130

Arg Gly Asp Xaa Xaa
 1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dbu-N-FCA-Aha (gamma amino group of Dbu
``` modified with fluoresceincarbonyl-amino-hexanoyl)

<400> SEQUENCE: 131

Arg Gly Asp Xaa Xaa
 1               5

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dbu-N-FCA-Aha (gamma amino group of Dbu
      modified with fluoresceincarbonyl-aminohexanoyl)

<400> SEQUENCE: 132

Arg Gly Asp Xaa Xaa
 1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dpr-N-FCA-Aha (beta amino group of Dpr
      modified with fluoresceincarbonyl-aminohexanoyl)

<400> SEQUENCE: 133

Arg Gly Asp Xaa Xaa
 1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dpr-N-FCA-Aha (beta amino group of Dpr modified
      with fluoresceincarbonyl-amino-hexanoyl)

<400> SEQUENCE: 134

Arg Gly Asp Xaa Xaa
 1               5

<210> SEQ ID NO 135
<211> LENGTH: 5

```
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dpr-N-FCA-Aha (beta amino group of Dpr modified
      with fluoresceincarbonyl-aminohexanoyl)

<400> SEQUENCE: 135

Arg Gly Asp Xaa Xaa
 1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Dpr-N-FCA-Aha (beta amino group of D-Dpr
      modified with fluoresceincarbonyl-aminohexanoyl)

<400> SEQUENCE: 136

Arg Gly Asp Xaa Xaa
 1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Dpr-N-FCA-Aha (beta amino group of D-Dpr
      modified with fluoresceincarbonyl-aminohexanoyl)

<400> SEQUENCE: 137

Arg Gly Asp Xaa Xaa
 1               5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
```

```
<221> NAME/KEY: MOD_RES
<222> LOCATION: (5)
<223> OTHER INFORMATION: D-Dpr-N-FCA-Aha (beta amino group of D-Dpr
      modified with fluoresceincarbonyl-aminohexanoyl)

<400> SEQUENCE: 138

Arg Gly Asp Xaa Xaa
 1               5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Lys-N-AcSal-Aha (epsilon amino group of Lys
      modified with acetylsalicyloyl-amino-hexanoyl)

<400> SEQUENCE: 139

Arg Gly Asp Xaa Xaa
 1               5

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Lys-N-AcSal-Aha (epsilon amino group of Lys
      modified with Acetylsalicyloyl-aminohexanoyl)

<400> SEQUENCE: 140

Arg Gly Asp Xaa Xaa
 1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Lys-N-AcSalAh (epsilon amino group of D-Lys
      modified with acetylsalicyloyl-amino-hexanoyl)

<400> SEQUENCE: 141

Arg Gly Asp Xaa Xaa
 1               5
```

```
<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Cys-S-AcSal-Aha (thiol group of Cys modified
      with acetylsalicyloyl-amino-hexanoyl)

<400> SEQUENCE: 142

Arg Gly Asp Xaa Xaa
 1               5

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dbu-N-AcSal-Aha (gamma amino group of Dbu
      modified with acetylsalicyloyl-aminohexan...)

<400> SEQUENCE: 143

Arg Gly Asp Xaa Xaa
 1               5

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Cys-S-AcSal-A (thiol group of D-Cys modified
      with acetylsalicyloyl-aminohexanoyl)

<400> SEQUENCE: 144

Arg Gly Asp Xaa Xaa
 1               5

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
```

```
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Cys-S-AcSal-A (thiol group of D-Cys modified
      with acetylsalicyloyl-amino-hexanoyl)

<400> SEQUENCE: 145

Arg Gly Asp Xaa Xaa
 1               5

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-AcSal-A (epsilon amino group of D-Lys
      modified with acetylsalicyloyl-amino-hexanoyl)

<400> SEQUENCE: 146

Arg Gly Asp Phe Xaa
 1               5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-AcSal-A (epsilon amino group of D-Lys
      modified with acetylsalicyloyl-aminohexanoyl)

<400> SEQUENCE: 147

Arg Gly Asp Trp Xaa
 1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys-N-AcSal-A (epsilon amino group of D-Lys
      modified with acetylsalicyloyl-aminohexanoyl)

<400> SEQUENCE: 148

Arg Gly Asp Tyr Xaa
 1               5

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
```

```
<221> NAME/KEY: MOD_RES
<222> LOCATION: (5)
<223> OTHER INFORMATION: D-Cys-S-AcSal-A (thiol group of D-Cys modified
      with acetylsalicyloyl-aminohexanoyl)

<400> SEQUENCE: 149

Arg Gly Asp Phe Xaa
 1               5

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: Dbu-N-AcSal-Aha (gamma amino group of Dbu
      modified with acetylsalicyloyl-aminohexan...)

<400> SEQUENCE: 150

Arg Gly Asp Phe Xaa
 1               5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-AcSal-A (thiol group of D-cys modified
      with acetylsalicyloyl-amino-hexanoyl)

<400> SEQUENCE: 151

Arg Gly Asp Trp Xaa
 1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys-S-AcSal-A (thiol group of D-Cys modified
      with acetylsalicyloylamino-hexanoyl)

<400> SEQUENCE: 152

Arg Gly Asp Tyr Xaa
 1               5

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
```

```
<220> FEATURE:
<221> NAME/KEY: MOD_RES
<222> LOCATION: (5)
<223> OTHER INFORMATION: Orn-N-AcSal-Aha (delta amino group of Orn
      modified with acteylsalicyloyl-aminohexan...)

<400> SEQUENCE: 153

Arg Gly Asp Xaa Xaa
 1               5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Orn-N-AcSal-Aha (delta amino group of Orn
      modified with acetylsalicyloyl-aminohexan...)

<400> SEQUENCE: 154

Arg Gly Asp Xaa Xaa
 1               5

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Orn-N-AcSal-Aha (delta amino group of Orn
      modified with acetylsalicyloyl-aminohexan...)

<400> SEQUENCE: 155

Arg Gly Asp Xaa Xaa
 1               5

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Orn-N-AcSal-A (delta amino group of D-Orn
      modified with acetylsalicyloyl-aminohexanoyl)

<400> SEQUENCE: 156

Arg Gly Asp Xaa Xaa
 1               5
```

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Orn-N-AcSal-A (delta amino group of D-Orn
      modified with acetylsalicyloyl-aminohexanoyl)

<400> SEQUENCE: 157

Arg Gly Asp Xaa Xaa
 1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Orn-N-AcSal-A (delta amino group of D-Orn
      modified with acetylsalicyloyl-aminohexanoyl)

<400> SEQUENCE: 158

Arg Gly Asp Xaa Xaa
 1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dbu-N-AcSal-Aha (gamma amino group of Dbu
      modified with acetylsalicyloyl-aminohexan...)

<400> SEQUENCE: 159

Arg Gly Asp Xaa Xaa
 1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:

```
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dbu-N-AcSal-Aha (gamma amino group of Dbu
      modified with acetylsalicyloyl-aminohexan...)

<400> SEQUENCE: 160

Arg Gly Asp Xaa Xaa
 1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-trp
<220> FEATURE:
<221> NAME/KEY: MOD_RES
<222> LOCATION: (5)
<223> OTHER INFORMATION: Dpr-N-AcSal-Aha (beta amino group of Dpr
      modified with acetylsalicyloyl-aminohexanoyl)

<400> SEQUENCE: 161

Arg Gly Asp Xaa Xaa
 1               5

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-tyr
<220> FEATURE:
<221> NAME/KEY: MOD_RES
<222> LOCATION: (5)
<223> OTHER INFORMATION: Dpr-N-AcSal-Aha (beta amino group of Dpr
      modified with acetylsalicyloyl-aminohexanoyl)

<400> SEQUENCE: 162

Arg Gly Asp Xaa Xaa
 1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dpr-N-AcSal-Aha (beta amino group of Dpr
      modified with acetylsalicyloyl-aminohexanoyl)

<400> SEQUENCE: 163
```

Arg Gly Asp Xaa Xaa
 1               5

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Dpr-N-AcSal-A (beta amino group of D-Dpr
      modified with acetylsalicyloyl-aminohexa...)

<400> SEQUENCE: 164

Arg Gly Asp Xaa Xaa
 1               5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Dpr-N-AcSal-A (beta amino group of D-Dpr
      modified with acetylsalicyloyl-aminohexa...)

<400> SEQUENCE: 165

Arg Gly Asp Xaa Xaa
 1               5

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Dpr-N-AcSal-A (beta amino group of D-Dpr
      modified with acetylsalicyloyl-aminohexa...)

<400> SEQUENCE: 166

Arg Gly Asp Xaa Xaa
 1               5

<210> SEQ ID NO 167
<211> LENGTH: 5
<212> TYPE: PRT
<213> ORGANISM: Artificial Sequence
<220> FEATURE:

```
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-HSEtCO (epsilon amino group of Lys
      modified with mercaptopropionyl)

<400> SEQUENCE: 167

Arg Gly Asp Xaa Xaa
  1               5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-CO-sucOMe (epsilon amino group of Lys
      modified with MeO-CO-(CH2)2-CO)

<400> SEQUENCE: 168

Arg Gly Asp Xaa Xaa
  1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-CO-suc-OH (epsilon amino group of Lys
      modified with HOOC-(CH2)2-CO-)

<400> SEQUENCE: 169

Arg Gly Asp Xaa Xaa
  1               5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-R1 (epsilon amino group of Lys modified
```

```
         with R2-CO-(CH2)2-CO-, wherein R2 is
         cyclo-(Arg-Gly-Asp-D-Phe-Lys-(N-epsilon-)-Gly))

<400> SEQUENCE: 170

Arg Gly Asp Xaa Xaa
 1               5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-R1 (epsilon amino group of Lys modified
      with cyclo(Arg-Gly-Asp-D-Phe-Lys)-CO-CH2-CH2-CO-)

<400> SEQUENCE: 171

Arg Gly Asp Xaa Xaa
 1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys-N-R1 (epsilon amino group of Lys modified
      with cyclo(Arg-Gly-Asp-D-Phe-Lys(N-epsilon)-CO-(CH2)2-S-S-
      (CH2)2-CO-))

<400> SEQUENCE: 172

Arg Gly Asp Xaa Xaa
 1               5

<210> SEQ ID NO 173
<211> LENGTH: 4
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: any single amino acid or a di, tri, or tetra
      peptide.

<400> SEQUENCE: 173

Arg Gly Asp Xaa
 1

<210> SEQ ID NO 174
<211> LENGTH: 5
<212> TYPE: PRT
<213> ORGANISM: Artificial Sequence
```

```
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Xaa is preferably dap, ser cys, asp D-asp,
      dab, homoserine homocystine, glu, D-glu thr, orn, lys, D-lys
      4-aminomethyl-phe or 4-aminomethyl-D-phe.

<400> SEQUENCE: 174

Xaa Pro Ala Ser Ser
 1               5

<210> SEQ ID NO 175
<211> LENGTH: 4
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: Xaa is preferably dap, ser cys, asp D-asp,
      dab, homoserine homocystine, glu, D-glu thr, orn, lys, D-lys
      4-aminomethyl-phe or 4-aminomethyl-D-phe.

<400> SEQUENCE: 175

Arg Gly Asp Xaa
 1

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe

<400> SEQUENCE: 176

Arg Gly Asp Xaa Lys
 1               5

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Arg(Mtr)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys(Boc)

<400> SEQUENCE: 177
```

```
Xaa Gly Xaa Xaa Xaa
 1               5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe

<400> SEQUENCE: 178

Arg Gly Asp Xaa Lys Gly
 1               5

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Arg(Mtr)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys(Boc)

<400> SEQUENCE: 179

Xaa Gly Xaa Xaa Xaa Gly
 1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe

<400> SEQUENCE: 180

Arg Gly Asp Xaa Val Lys
 1               5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
```

```
<221> NAME/KEY: MOD_RES
<222> LOCATION: (1)
<223> OTHER INFORMATION: Arg(Mtr)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (6)
<223> OTHER INFORMATION: Lys(Boc)

<400> SEQUENCE: 181

Xaa Gly Xaa Xaa Val Xaa
 1               5

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp

<400> SEQUENCE: 182

Arg Gly Asp Xaa Lys
 1               5

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr

<400> SEQUENCE: 183

Arg Gly Asp Xaa Lys
 1               5

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Lys

<400> SEQUENCE: 184

Arg Gly Asp Xaa Xaa
 1               5
```

```
<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe

<400> SEQUENCE: 185

Arg Gly Asp Xaa Cys
 1               5

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dab

<400> SEQUENCE: 186

Arg Gly Asp Xaa Xaa
 1               5

<210> SEQ ID NO 187
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Cys

<400> SEQUENCE: 187

Arg Gly Asp Xaa Xaa
 1               5

<210> SEQ ID NO 188
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Cys
```

<400> SEQUENCE: 188

Arg Gly Asp Xaa Xaa
 1               5

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys

<400> SEQUENCE: 189

Arg Gly Asp Phe Xaa
 1               5

<210> SEQ ID NO 190
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys

<400> SEQUENCE: 190

Arg Gly Asp Trp Xaa
 1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Lys

<400> SEQUENCE: 191

Arg Gly Asp Tyr Xaa
 1               5

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys

<400> SEQUENCE: 192

Arg Gly Asp Phe Xaa
 1               5

<210> SEQ ID NO 193

```
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: Dab

<400> SEQUENCE: 193

Arg Gly Asp Phe Xaa
 1               5

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys

<400> SEQUENCE: 194

Arg Gly Asp Trp Xaa
 1               5

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (5)
<223> OTHER INFORMATION: D-Cys

<400> SEQUENCE: 195

Arg Gly Asp Tyr Xaa
 1               5

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Orn

<400> SEQUENCE: 196

Arg Gly Asp Xaa Xaa
 1               5

<210> SEQ ID NO 197
<211> LENGTH: 5
<212> TYPE: PRT
<213> ORGANISM: Artificial Sequence
```

```
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Orn

<400> SEQUENCE: 197

Arg Gly Asp Xaa Xaa
 1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Orn

<400> SEQUENCE: 198

Arg Gly Asp Xaa Xaa
 1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Orn

<400> SEQUENCE: 199

Arg Gly Asp Xaa Xaa
 1               5

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Orn

<400> SEQUENCE: 200
```

Arg Gly Asp Xaa Xaa
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-Orn

<400> SEQUENCE: 201

Arg Gly Asp Xaa Xaa
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dab

<400> SEQUENCE: 202

Arg Gly Asp Xaa Xaa
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dab

<400> SEQUENCE: 203

Arg Gly Asp Xaa Xaa
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:

```
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Dap

<400> SEQUENCE: 204

Arg Gly Asp Xaa Xaa
 1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: Dap

<400> SEQUENCE: 205

Arg Gly Asp Xaa Xaa
 1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Dap

<400> SEQUENCE: 206

Arg Gly Asp Xaa Xaa
 1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: D-Dap

<400> SEQUENCE: 207

Arg Gly Asp Xaa Xaa
 1               5
```

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Tyr
<220> FEATURE:
<221> NAME/KEY: MOD_RES
<222> LOCATION: (5)
<223> OTHER INFORMATION: D-Dap

<400> SEQUENCE: 208

Arg Gly Asp Xaa Xaa
 1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: D-dap

<400> SEQUENCE: 209

Arg Gly Asp Xaa Xaa
 1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: epsilon amino group of Lys modified with
      (SuN-O-CO-(CH2)2-CO)

<400> SEQUENCE: 210

Arg Gly Asp Xaa Xaa
 1               5

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Arg(Mtr)

```
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: Lys(CBZ)

<400> SEQUENCE: 211

Xaa Gly Xaa Xaa Xaa
 1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Arg(Mtr)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe

<400> SEQUENCE: 212

Xaa Gly Xaa Xaa Lys
 1               5

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Arg(Mtr)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: epsilon amino group of Lys modified with
      (CO-(CH2)2-COOH)

<400> SEQUENCE: 213

Xaa Gly Xaa Xaa Xaa
 1               5

<210> SEQ ID NO 214
<211> LENGTH: 10
<212> TYPE: PRT
```

```
<213> ORGANISM: Artificial Sequence
<220> FEATURE:
<223> OTHER INFORMATION: Description of Artificial Sequence:
      cyclopeptide derivative
<220> FEATURE:
<221> NAME/KEY: MOD_RES
<222> LOCATION: (1)
<223> OTHER INFORMATION: Arg(Mtr)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: D-Phe
<220> FEATURE:
<221> NAME/KEY: MOD_RES
<222> LOCATION: (5)
<223> OTHER INFORMATION: epsilon amino group of Lys modified with
      (CO-(CH2)2-CO)
<220> FEATURE:
<221> NAME/KEY: MOD_RES
<222> LOCATION: (6)
<223> OTHER INFORMATION: Arg(Mtr)
<220> FEATURE:
<221> NAME/KEY: MOD_RES
<222> LOCATION: (8)
<223> OTHER INFORMATION: Asp(OBut)
<220> FEATURE:
<221> NAME/KEY: MOD_RES
<222> LOCATION: (9)
<223> OTHER INFORMATION: D-Phe
<220> FEATURE:
<221> NAME/KEY: MOD_RES
<222> LOCATION: (10)
<223> OTHER INFORMATION: epsilon amino group of Lys modified with
      (CO-(CH2)2-CO)

<400> SEQUENCE: 214

Xaa Gly Xaa Xaa Xaa Xaa Gly Xaa Xaa Xaa
 1               5                  10
```

CYCLOPEPTIDE DERIVATIVES

The invention relates to compounds of the formula I

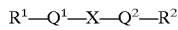     I in which
- $Q^1$, $Q^2$ are, in each case independently of each other, either absent or —NH—$(CH_2)_n$—CO—,
- $R^1$, $R^2$ are, in each case independently of each other, either absent or cyclo-(Arg-Gly-Asp-Z)(SEQ ID NO: 173), where Z is bonded in the side chain to $Q^1$ or $Q^2$ or, if $Q^1$ and/or $Q^2$ is/are absent, to X, and where at least one of the radicals $R^1$ or $R^2$ must always be present,

- X is —CO—$R^{18}$—CO—, and if $R^1$—$Q^1$— or $R^2$—$Q^2$— is absent, $R^{10}$, $R^{13}$, $R^{16}$, Het-CO or a fluorescent dye residue which is linked by way of a —CONH—, —COO—, —NH—C(=S)—NH—, —NH—C(O)—NH—, —SO$_2$NH— or —NHCO— bond,
- Z is, in each case independently of each other, an amino acid residue or a di-, tri- or tetra-peptide residue, where the amino acids are selected, independently of each other, from a group consisting of Ala, Asn, Asp, Arg, Cys, Gln, Glu, Gly, His, Ile, Leu, Lys, Met, Phe, Pro, Ser, Thr, Trp, Tyr, Val or M,
  - where the said amino acids can also be derivatized and the amino acid residues are linked to each other, in peptide manner, by way of the α-amino and α-carboxyl groups, and
  - where M is always present,
- M is NH($R^8$)—CH($R^3$)—COOH,
- $R^3$ is —$R^5$—$R^4$, —$R^6$—$R^4$ or —$R^7$—$R^4$,
- $R^4$ is OH, NH$_2$, SH or COOH,
- $R^5$ is alkylene having 1–6 carbon atoms,
- $R^6$ is alkylenephenylene having 7–14 carbon atoms,
- $R^7$ is alkylenephenylalkylene having 8–15 carbon atoms,
- $R^8$ is H, A or alkylenephenyl having 7–12 carbon atoms,
- A is alkyl having 1–6 carbon atoms,
- $R^{10}$ is alkanoyl having 1–18 carbon atoms which is unsubstituted or substituted once by COOH, COOA, SR$^{11}$ or NR$^{12}$R$^{12'}$,
- $R^{11}$ is H or trityl, pyridyl-2-thio or alkylthio having 1–6 carbon atoms,
- $R^{12}$, $R^{12'}$ are, in each case independently of each other, H, alkyl having 1–8 carbon atoms or an amino-protecting group,
- $R^{13}$ is aroyl having 7–11 carbon atoms which is unsubstituted or substituted once or twice by alkyl having 1–6 carbon atoms, alkoxy having 1–4 carbon atoms, alkanoyl having 1–8 carbon atoms, Hal, SR$^{14}$ or NR$^{15}$R$^{15'}$,
- $R^{14}$ is H or A,
- $R^{15}$, $R^{15'}$ are, in each case independently of each other, H or A,
- $R^{16}$ is aralkanoyl having 7–19 carbon atoms which is unsubstituted or substituted once, twice or three times in the aryl moiety by Hal, alkoxy having 1–6 carbon atoms or OH and in which the aryl moiety can also be a

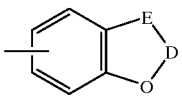

group,
- E is CH$_2$ or O,
- D is carbonyl or [C(R$^{17}$R$^{17'}$)]$_m$,
- $R^{17}$, $R^{17'}$ are, in each case independently of each other, H or A,
- $R^{18}$ is absent, or is $R^{19}$, $R^{20}$, $R^{19}$—$R^{20}$—$R^{19}$, or phenylene which is unsubstituted or substituted once or twice by $R^5$, where the chain length of $R^5$ is in each case independent of each other,
- $R^{19}$ is alkylene having 1–8 carbon atoms, where 1 or 2 methylene groups can be replaced by S, —CH=CH— or —C≡C—,
- $R^{20}$ is cycloalkylene having 3–7 carbon atoms,
- Hal is F, Cl, Br or I,
- Het is a mononuclear or binuclear saturated, unsaturated or aromatic heterocycle having from 1 to 4 N, O and/or S atoms, bonded via N or C, which can be unsubstituted or substituted once, twice or three times by Hal, A, R$^3$, NR$^4$R$^{4'}$, CN, NO$_2$ and/or carbonyl oxygen,
- n is 1, 2, 3, 4, 5, 6, 7, 8, 9 or 10, and
- m is 1 or 2, where, provided that the residues are residues of optically active amino acids and amino acid derivatives, both the D and the L forms are included, and the salts thereof.

Similar compounds of cyclic peptides are disclosed in DE 43 10 643.

The invention was based on the object of discovering novel compounds possessing valuable properties, in particular those compounds which can be used for preparing pharmaceuticals.

It was found that the compounds of the formula I, and their salts, possess very valuable pharmacological properties while being well tolerated. In particular, they act as integrin inhibitors, in which connection they particularly inhibit the interactions of the $α_v$-, $β_3$- or $β_5$-integrin receptors with ligands, such as the binding of fibrinogen to the $β_3$-integrin receptor. The compounds exhibit particular activity in the case of the $α_vβ_3$, $α_vβ_5$ and $α_{IIb}β_3$ integrins and also the $α_vβ_1$, $α_vβ_6$ and $α_vβ_8$ integrins. This effect can be demonstrated, for example, using the method described by J. W. Smith et al. in J. Biol. Chem. 265, 12267–12271 (1990). PC Brooks, R. A. Clark and D. A. Cheresh have reported, in Science 264, 569–71 (1994), that the development of angiogenesis depends on the interaction between vascular integrins and extracellular matrix proteins.

The possibility of using a cyclic peptide to inhibit this interaction, and thereby initiate apoptosis (programmed cell death) of angiogenic vascular cells, has been described by P. C. Brooks, A. M. Montgomery, M. Rosenfeld, R. A. Reisfeld, T.-Hu, G. Klier and D. A. Cheresh in Cell 79, 1157–64 (1994).

Compounds of the formula I, which block the interaction of integrin receptors and ligands, such as that of fibrinogen to the fibrinogen receptor (Glycoprotein IIb/IIIa), prevent, as GPIIb/IIIa antagonists, the spread of tumour cells as a result of metastasis. This is substantiated by the following observations:

The compounds can inhibit the binding of metalloproteinases to integrines and thereby prevent the cells from being able to use the enzymatic activity of the proteinase. An example is provided by the ability of a cyclo-RGD peptide to inhibit the binding of MMP 2 (matrix metalloproteinase 2) to the vitro-nectin receptor $\alpha_v\beta_3$, as described in P. C. Brooks et al., Cell 85, 683–693 (1996).

The spread of tumour cells from a local tumour into the vascular system takes place by the formation of microaggregates (microthrombi) as a result of the interaction of the tumour cells with blood platelets. The tumour cells are shielded as a result of the protection afforded by the microaggregate and are not recognized by the cells of the immune system. The microaggregates can settle on vessel walls, thereby facilitating further penetration of tumour cells into the tissue. Since the formation of the microthrombi is mediated by the binding of fibrinogen to the fibrinogen receptors on activated blood platelets, the GPIIa/IIIb antagonists can be regarded as effective inhibitors of metastasis.

The compounds of the formula I may be employed as pharmaceutical active compounds in human and veterinary medicine, in particular for the prophylaxis and/or therapy of thrombosis, myocardial infarct, arteriosclerosis, inflammations, stroke, angina pectoris, tumour diseases, osteolytic diseases such as osteoporosis, pathologically angiogenic diseases such as inflammations, ophthalmological diseases, diabetic retinopathy, macular degeneration, myopia, ocular histoplasmosis, rheumatic arthritis, osteoarthritis, rubeotic glaucoma, ulcerative colitis, Crohn's disease, atherosclerosis, psoriasis, restenosis following angioplasty, viral infection, bacterial infection, fungal infection, in acute liver failure and for supporting the healing processes in wound healing.

The compounds of the formula I may be employed as substances having an antimicrobial effect in operations in which biomaterials, implants, catheters or heart pacemakers are used. In this context, they have an antiseptic effect. The efficacy of the antimicrobial activity can be demonstrated using the method described by P. Valentin-Weigund et al., in Infection and Immunity, 2851–2855 (1988).

The amino acid residue abbreviations which are cited in the above text and in that which follows represent the residues of the following amino acids:

| Abu | 4-Aminobutyric acid |
| Aha | 6-Aminohexanoic acid, 6-aminocaproic acid |
| Ala | Alanine |
| Asn | Asparagine |
| Asp | Aspartic acid |
| Arg | Arginine |
| Cys | Cysteine |
| Dab | 2,4-Diaminobutyric acid |
| Dap | 2,3-Diaminopropionic acid |
| Gln | Glutamine |
| Glp | Pyroglutamic acid |
| Glu | Glutamic acid |
| Gly | Glycine |
| His | Histidine |
| homo-Phe | homo-Phenylalanine |
| Ile | Isoleucine |
| Leu | Leucine |
| Lys | Lysine |
| Met | Methionine |
| Nle | Norleucine |
| Orn | Ornithine |
| Phe | Phenylalanine |
| Phg | Phenylglycine |
| 4-Hal-Phe | 4-Halo-phenylalanine |
| Pro | Proline |
| Ser | Serine |

-continued

| Thr | Threonine |
| Trp | Tryptophan |
| Tyr | Tyrosine |
| Val | Valine. |

In addition, the abbreviations below have the following meanings:

| Ac | Acetyl |
| BOC | tert-Butoxycarbonyl |
| CBZ or Z | Benzyloxycarbonyl |
| DCCI | Dicyclohexylcarbodiimide |
| DMF | Dimethylformamide |
| EDCI | N-Ethyl-N,N'-(dimethylaminopropyl)carbodiimide |
| Et | Ethyl |
| FCA | Fluoresceincarboxylic acid |
| FITC | Fluorescein isothiocyanate |
| Fmoc | 9-Fluorenylmethoxycarbonyl |
| FTH | Fluorescein thiourea |
| HOBt | 1-Hydroxybenzotriazole |
| Me | Methyl |
| MBHA | 4-Methylbenzhydrylamine |
| Mtr | 4-Methoxy-2,3,6-trimethylphenylsulphonyl |
| HONSu | N-Hydroxysuccinimide |
| OBut | tert-Butyl ester |
| Oct | Octanoyl |
| OMe | Methyl ester |
| OEt | Ethyl ester |
| POA | Phenoxyacetyl |
| Sal | Salicyloyl |
| TFA | Trifluoroacetic acid |
| Trt | Trityl (triphenylmethyl) |

Provided that the abovementioned amino acids are able to appear in several enantiomeric forms, all these forms, and also their mixtures (for example the DL forms) are included both above and below, for example as an integral part of the compounds of the formula I. In addition, the amino acids can, for example as an integral part of compounds of the formula I, be provided with appropriate protecting groups which are known per se.

The compounds according to the invention also include so-called prodrug derivatives, that is compounds of the formula I which are modified with, for example, alkyl or acyl groups, sugars or oligopeptides, and which are rapidly cleaved in the organism to give the effective compounds according to the invention. This also includes biodegradable polymer derivatives of the compounds according to the invention, as described, for example, in Int. J. Pharm. 115, 61–67 (1995).

The invention furthermore relates to a process for preparing compounds of the formula I according to claim 1, and their salts, characterized in that (a) a compound of the formula II

     II in which
Q¹ and R¹ have the meaning given in claim 1, is reacted, in an acylation reaction,
with a compound of the formula III

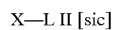     III in which
X has the meaning given in claim 1, and
L is Cl, Br, I or a free or reactive functionally modified OH group, or b) in that a compound of the formula IV $$H—Q^2—R^2 \qquad\qquad IV$$

in which
Q² and R² have the meaning given in claim 1, is reacted, in an acylation reaction, with a compound of the formula V $$R^1—Q^1—X—L \qquad\qquad V$$

in which
R¹, Q¹, X and L have the given meaning, or c) in that a compound of the formula II $$H—Q^1—R^1 \qquad\qquad II$$

in which
Q¹ and R¹ have the meaning given in claim 1, is reacted, in an addition reaction, with a compound of the formula VI $$X—U \qquad\qquad VI$$

in which
X has the meaning given in claim 1, and
U is —N=C=O, —N=C=S or maleimidyl, or d) in that they are liberated from one of their functional derivatives by treatment with a solvolysing or hydrogenolysing agent, and/or in that a basic or acidic compound of the formula I is converted into one of its salts by treatment with an acid or base.

In the above text, and in that which follows, the radicals $Q^1$, $Q^2$, $R^1$, $R^2$, X and L have the meanings given in the formulae I, II and III provided another alternative is not expressly indicated.

In the above formulae, alkyl is preferably methyl, ethyl, propyl, isopropyl, butyl, isobutyl, sec-butyl or tert-butyl, and, in addition, also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, or 1,1,2- or 1,2,2-trimethylpropyl.

Alkylene is preferably methylene, ethylene, propylene, butylene, pentylene or hexylene. Alkylenephenyl is preferably benzyl or phenethyl. Alkylenephenylalkylene is preferably 4-methylenebenzyl or 4-ethylenebenzyl.

$Q^1$ and $Q^2$ are preferably, in each case independently of each other, 6-aminohexanoic acid (6-aminocaproic acid) or are absent, where, preferably, for example $Q^1$ is 6-aminohexanoic acid and $Q^2$ is absent.

M is preferably Dap, Ser, Cys, Asp, D-Asp, Dab, homoserine, homocysteine, Glu, D-Glu, Thr, Orn, Lys, D-Lys, 4-aminomethyl-Phe or 4-aminomethyl-D-Phe.

The amino acids and amino acid residues which are mentioned for Z in the meanings can also be derivatized, with the N-methyl, N-ethyl, N-propyl, N-benzyl or $C_\alpha$-methyl derivatives being preferred.

Preference is also given to derivatives of Asp and Glu, in particular the methyl, ethyl, propyl, butyl, tert-butyl, neopentyl or benzyl esters of the side-chain carboxyl groups, and also to derivatives of Arg, which can be substituted on the —NH—C(=NH)—NH₂ group by an acetyl, benzoyl, methoxycarbonyl or ethoxycarbonyl radical.

Z is preferably M, with preference also being given to D-Phe-M, D-Trp-M, D-Tyr-M, D-Phe-Lys, D-Phe-D-Lys, D-Trp-Lys, D-Trp-D-Lys, D-Tyr-Lys, D-Tyr-D-Lys, D-Phe-Orn, D-Phe-Dab, D-Phe-Dap, D-Phe-D-Orn, D-Phe-D-Dab, D-Phe-D-Dap, D-Phe-4-aminomethyl-Phe, D-Phe-4-aminomethyl-D-Phe, D-Trp-4-aminomethyl-Phe, D-Trp-4-aminomethyl-D-Phe, D-Tyr-4-aminomethyl-Phe, D-Tyr-4-aminomethyl-D-Phe, D-Phe-Asp, D-Phe-D-Asp, D-Trp-Asp, D-Trp-D-Asp, D-Tyr-Asp, D-Tyr-D-Asp, D-Phe-Cys, D-Phe-D-Cys, D-Trp-Cys, D-Trp-D-Cys, D-Tyr-Cys, D-Tyr-D-Cys, Phe-D-Lys, Trp-D-Lys, Tyr-D-Lys, Phe-Orn, Phe-Dab, Phe-Dap, Trp-Orn, Trp-Dab, Trp-Dap, Tyr-Orn, Tyr-Dab, Tyr-Dap, Phe-4-aminomethyl-D-Phe, Trp-4-aminomethyl-D-Phe, Tyr-4-aminomethyl-D-Phe, Phe-D-Asp, Trp-D-Asp, Tyr-D-Asp, Phe-D-Cys, Trp-D-Cys, Tyr-D-Cys, D-Phe-Lys-Gly, D-Phe-M-Gly, D-Trp-Lys-Gly, D-Trp-M-Gly, D-Tyr-Lys-Gly, D-Tyr-M-Gly, D-Phe-Val-Lys, D-Phe-Gly-Lys, D-Phe-Ala-Lys, D-Phe-Ile-Lys, D-Phe-Leu-Lys, D-Trp-Val-Lys, D-Trp-Gly-Lys, D-Trp-Ala-Lys, D-Trp-Ile-Lys, D-Trp-Leu-Lys, D-Tyr-Val-Lys, D-Tyr-Gly-Lys, D-Tyr-Ala-Lys, D-Tyr-Ile-Lys, D-Tyr-Leu-Lys, and also M-Pro-Ala-Ser-Ser. (SEQ ID NO: 174).

The radical —$R^6$—$R^4$ is preferably 2-, 3- or 4-hydroxybenzyl, 2-, 3- or 4-aminobenzyl, 2-, 3- or 4-mercaptobenzyl, 2-, 3- or 4-carboxybenzyl, and also, preferably, 2-, 3- or 4-hydroxyphenethyl, 2-, 3- or 4-aminophenethyl, 2-, 3- or 4-mercaptophenethyl or 2-, 3- or 4-carboxyphenethyl.

Alkanoyl is preferably formyl, acetyl, propionyl, butyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

Aroyl is preferably benzoyl or naphthoyl.

$R^{13}$ is unsubstituted, preferably—as indicated—monosubstituted benzoyl, with individual preference being given to benzoyl, o-, m- or p-methylbenzoyl, o-, m- or p-ethylbenzoyl, o-, m- or p-propylbenzoyl, o-, m- or p-isopropylbenzoyl, o-, m- or p-tert-butylbenzoyl, o-, m- or p-aminobenzoyl, o-, m- or p-(N-methylamino)-benzoyl, o-, m- or p-methoxybenzoyl, o-, m- or p-ethoxybenzoyl, o-, m- or p-(N,N,dimethylamino)-benzoyl, o-, m- or p-(N-ethylamino)-benzoyl, o-, m- or p-(N,N-diethylamino)-benzoyl, o-, m- or p-fluorobenzoyl, o-, m- or p-bromobenzoyl, o-, m- or p-chlorobenzoyl, o-, m- or p-formylbenzoyl, o-, m- or p-acetylbenzoyl, o-, m- or p-propionylbenzoyl, o-, m- or p-butyrylbenzoyl, o-, m- or p-pentanoylbenzoyl, o-, m- or p-methylthiobenzoyl, with preference also being given to 2,3-, 2,4-, 2,5-, 2,6-, 3,4- or 3,5-difluorobenzoyl, 2,3-, 2,4-, 2,5-, 2,6-, 3,4- or 3,5-dichlorobenzoyl, 2,3-, 2,4-, 2,5-, 2,6-, 3,4- or 3,5-dibromobenzoyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorobenzoyl, 2-bromo-3-methyl-, 2-bromo-4-methyl-, 2-bromo-5-methyl-, 2-bromo-6-methyl-, 2-methyl-3-bromo-2-methyl-4-bromo-, 2-methyl-5-bromo-, 2-methyl-6-bromo-, 3-bromo-4-methyl-, 3-bromo-5-methyl- or 3-methyl-4-bromobenzoyl, or 2,5- or 3,4-dimethoxybenzoyl.

$R^{16}$ is unsubstituted, preferably—as indicated—monosubstituted phenylacetyl, with individual preference being given to phenylacetyl, o-, m- or p-methoxyphenylacetyl, o-, m- or p-hydroxyphenylacetyl, o-, m- or p-ethoxyphenylacetyl, o-, m- or p-fluorophenylacetyl, o-, m- or p-bromophenylacetyl, o-, m- or p-chlorophenylacetyl, with preference also being given to 3-phenylpropionyl, 4-phenylbutyryl, 5-phenylpentanoyl, 6-phenylhexanoyl, 7-phenylheptanoyl, 8-phenyloctanoyl, 9-phenylnonanoyl, 10-phenyldecanoyl, 11-phenylundecanoyl, 12-phenyldodecanoyl or 13-phenyltridecanoyl, and, in addition, 2,3-methylenedioxyphenyl, 3,4-methylenedioxyphenyl, 2,3-dihydrobenzofuranyl or 2,3-dihydro-2-oxobenzofuranyl.

Cycloalkylene is preferably cyclopropylene, 1,2- or 1,3-cyclobutylene, 1,2- or 1,3-cyclopentylene, 1,2-, 1,3- or 1,4-cyclohexylene and, in addition, 1,2-, 1,3- or 1,4-cycloheptylene.

D is preferably $CH_2$, with carbonyl also being preferred.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and preferably also 1,2,3-triazol-1-, -4- or -5-yl, 1,2,4-triazol-1-, -3- or 5-yl, 1- or 5-tetrazolyl, 1,2,3-oxadiazol-4- or 5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl or 2-, 4-, 5-, 6-, 7- or 8-quinazolinyl. The heterocyclic radicals can also be partially or completely hydrogenated. Het can consequently also, for example, be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

Amino-protecting group is preferably acetyl, propionyl, butyryl, phenylacetyl, benzoyl, toluyl, POA, methoxycarbonyl, ethoxycarbonyl, 2,2,2-trichloroethoxycarbonyl, BOC, 2-iodoethoxycarbonyl, CBZ ("carbobenzoxy"), 4-methoxybenzyloxycarbonyl, FMOC, Mtr or benzyl.

Fluorescent dye residue is preferably 7-acetoxycoumarin-3-yl, fluorescein-5-(and/or 6-)yl, 2',7'-dichlorofluorescein-5-(and 6-)yl, dihydrotetramethylrosamin-4-yl, tetramethylrhodamin-5- (and/or 6-)yl, 4,4-difluoro-5,7-dimethyl-4-bora-3a,4a-diaza-s-indacen-3-ethyl or 4,4-difluoro-5,7-diphenyl-4-bora-3a,4a-diaza-s-indacen-3-ethyl.

Suitable functionalized fluorescent dye residues which can be used as reagents for preparing the compounds according to the invention of the formula I are described, for example, in Handbook of Fluorescent Probes and Research Chemicals, 5th Edition, 1992–1994 by R. P. Haughland, Molecular Probes, Inc.

m is preferably 1, with 2 also being preferred.

Hal is preferably F, Cl or Br, and also I.

The compounds of formula I may possess one or more chiral centres and therefore occur in different stereoisomeric forms. The formula I encompasses all these forms.

Accordingly, the invention relates, in particular, to those compounds of the formula I in which at least one of the said radicals has one of the abovementioned preferred meanings. Some preferred groups of compounds may be expressed by the following partial formulae Ia to Ih, which correspond to the formula I and in which the radicals which are not specifically named have the meaning given in formula I, but in which

| | | |
|---|---|---|
| in a) | $Q^1$, $Q^2$ and $R^2$ | are absent, |
| | $R^1$ | is cyclo-(Arg-Gly-Asp-Z)(SEQ ID NO: 173), and |
| | X | is alkanoyl; |
| in b) | $Q^1$, $Q^2$ and $R^2$ | are absent, |
| | $R^1$ | is cyclo-(Arg-Gly-Asp-M)(SEQ ID NO: 175), and |
| | X | is alkanoyl; |
| in c) | $Q^1$, $Q^2$ and $R^2$ | are absent, |
| | $R^1$ | is cyclo-(Arg-Gly-Asp-D-Phe-Lys), (SEQ ID NO: 176) and |
| | X | is alkanoyl; |
| in d) | $Q^1$ and $Q^2$ | are absent, |
| | $R^1$ and $R^2$ | are cyclo-(Arg-Gly-Asp-D-Phe Lys), (SEQ ID NO: 176) and |
| | X | is —CO—$(CH_2)_n$—CO—; |
| in e) | $Q^2$ and $R^2$ | are absent, |
| | $Q^1$ | is —NH—$(CH_2)_5$—CO—, |
| | $R^1$ | is cyclo-(Arg-Gly-Asp-Z)(SEQ ID NO: 173), and |
| | X | is a fluorescent dye residue; |
| in f) | $Q^2$ and $R^2$ | are absent, |
| | $Q^1$ | is —NH—$(CH_2)_5$—CO—, |
| | $R^1$ | is cyclo-(Arg-Gly-Asp-M)(SEQ ID NO: 175), and |
| | X | is fluoresceinoyl; |
| in g) | $Q^1$ and $Q^2$ | are absent, |
| | $R^1$ and $R^2$ | are cyclo-(Arg-Gly-Asp-M)(SEQ ID NO: 173), and |
| | X | is —CO—$(CH_2)_8$—CO—; |
| in h) | $Q^1$, $Q^2$ and $R^2$ | are absent, |
| | $R^1$ | is cyclo-(Arg-Gly-Asp-Z)(SEQ ID NO: 173), and |
| | X | is $CH_3$—$(CH_2)_{16}$—CO—. |

Particular preference is given to compounds of the formula VII

Cyclo-(Arg-Gly-Asp-D-Phe-Lys($Q^1$—X))(SEQ ID NO: 176)  VII, in which $Q^1$ has the meaning given in claim 1, and where $Q^1$ is bonded to the side chain of the lysine, or, if $Q^1$ is absent, X is bonded to the side chain of the lysine, and in which X is preferably alkanoyl having 1–18 carbon atoms which is unsubstituted or substituted once by COOH, COOA, $SR^{14}$ or $NR^{15}R^{15'}$ FCA or FTH, or aroyl having 7–11 carbon atoms which is unsubstituted or substituted once or twice by alkyl having 1–6 carbon atoms, alkoxy having 1–4 carbon atoms, alkanoyl having 1–8 carbon atoms, Hal, $SR^{14}$ or $NR^{15}R^{15'}$, where $R^{14}$, $R^{15}$ and $R^{15'}$ have the meanings given in claim 1.

Otherwise, the compounds of the formula I, and also the starting compounds for preparing them, are prepared by methods which are known per se, as described in the literature (for example in the standard works such as Houben-Weyl, Methoden der organischen Chemie, [Methods of organic chemistry], Georg-Thieme-Verlag, Stuttgart;) specifically under reaction conditions which are known and suitable for the said reactions. In this context, use can also be made of variants which are known per se but which are not detailed here.

The starting compounds can, if desired, also be formed in situ, so that they are not isolated from the reaction mixture but, instead, immediately subjected to further reaction to give the compounds of the formula I.

Compounds of the formula I may preferably be obtained by reacting compounds of the formula II with compounds of the formula III.

As a rule, the compounds of the formula [sic] II and III are known. If they are not known, they can be prepared by methods which are known per se.

In the compounds of the formula III, the radical L is preferably a preactivated carboxylic acid, preferably a carbonyl halide, symmetrical or mixed anhydride or an active ester. Radicals of this nature for activating the carboxyl group in typical acylation reactions are described in the literature (for example in the standard works such as Houben-Weyl, Methoden der organischen Chemie [Methods of organic chemistry], Georg-Thieme-Verlag, Stuttgart). Activated esters are expediently formed in situ, for example by adding HOBt or N-hydroxysuccinimide.

L is preferably H, F, Cl, Br or —ON— succinimide.

As a rule, the reaction is carried out in an inert solvent in the presence of an acid-binding agent, preferably an organic base such as triethylamine, dimethylaniline, pyridine or quinoline, or of an excess of the carboxyl component of the formula III. It can also be advantageous to add an alkali metal or alkaline earth metal hydroxide, carbonate or bicarbonate or another salt of a weak acid of the alkali metals or alkaline earth metals, preferably of potassium, sodium, calcium or caesium. In each case depending on the conditions used, the reaction time is between a few minutes and 14 days, while the reaction temperature is between about −30° and 140°, normally between −10° and 90°, in particular between about 0° and about 70°.

Examples of suitable inert solvents are hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl ether or ethylene glycol monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulphoxides such as dimethyl sulphoxide (DMSO); carbon disulphide; carboxylic acids such as formic acid or acetic acid; nitro compounds such as nitromethane or nitrobenzene; esters such as ethyl acetate, water, or mixtures of the said solvents.

In addition, compounds of the formula I can be obtained by reacting compounds of the formula IV with compounds of the formula V. As a rule, the starting compounds of the formula IV and V are known. If they are not known, they can be prepared by methods which are known per se.

In the compounds of the formula V, the radical L is preferably a preactivated carboxylic acid, preferably a carbonyl halide, symmetrical or mixed anhydride or an active ester. Radicals of this nature for activating the carboxyl group in typical acylation reactions are described in the literature (for example in the standard works such as Houben-Weyl, Methoden der organischen Chemie, [Methods of organic chemistry], Georg-Thieme-Verlag, Stuttgart). L is preferably F, Cl, Br or —ON— succinimide.

The reaction of the compounds of the formula IV with compounds of the formula V is carried out under the same conditions, as regards the reaction time, the temperature and the solvent, as has been described for the reaction of the compounds of the formula II with compounds of the formula III.

In addition, compounds of the formula I can be obtained by reacting compounds of the formula II with compounds of the formula VI. As a rule, the starting compounds of the formula [sic] II and VI are known. If they are not known, they can be prepared by methods which are known per se. The reaction of compounds of the formula II with compounds of the formula III constitutes a typical addition to isothiocyanates. Additions of this nature are described in the literature (for example in the standard works such as Houben-Weyl, Methoden der organischen Chemie [Methods of organic chemistry], Georg-Thieme-Verlag, Stuttgart).

Cyclic compounds of the formula $R^1$ and/or $R^2$ can be prepared by cyclizing the linear compounds as, for example, described in DE 43 10 643 or in Houben-Weyl, I.c., Volume 15/II, pages 1 to 806 (1974).

The compounds of the formula I can furthermore be obtained by liberating them from their functional derivatives by means of solvolysis, in particular hydrolysis, or by hydrogenolysis.

Starting compounds which are preferred for the solvolysis or hydrogenolysis are those which, in place of one or more free amino and/or hydroxyl groups, contain corresponding, protected amino and/or hydroxyl groups, preferably those which carry an amino protecting group in place of an H atom which is bonded to an N atom, for example those which conform to the formula I but which contain an $NHR^1$ group (in which R' is an amino protecting group, for example BOC or CBZ) in place of an $NH_2$ group.

In addition, starting compounds are preferred which carry an hydroxyl-protecting group in place of the H atom of an hydroxyl group, for example those which conform to the formula I but which contain an R"O-phenyl group (in which R" is an hydroxyl-protecting group) in place of an hydroxyphenyl group.

Several—identical or different—protected amino and/or hydroxyl groups can also be present in the molecule of the starting compound. If the protecting groups which are present are different from each other, they can in many cases be eliminated selectively.

The expression "amino-protecting group" is well known and relates to groups which are suitable for protecting (blocking) an amino group from chemical reactions but which can readily be removed after the desired chemical reaction has been carried out at other sites in the molecule. Unsubstituted or substituted acyl, aryl, aralkoxymethyl or aralkyl groups are typical groups of this nature. Since the amino-protecting groups are removed after the desired reaction (or reaction sequence), their nature and size is otherwise not critical; however, those having 1–20, in particular 1–8, carbon atoms are preferred. In connection with the present process, the expression "acyl group" is to be understood in the broadest possible sense. It comprises acyl groups which are derived from aliphatic, araliphatic, aromatic or heterocyclic carboxylic acids or sulphonic acids, and also, in particular, alkoxycarbonyl, aryloxycarbonyl and, especially, aralkoxycarbonyl groups. Examples of acyl groups of this nature are alkanoyl such as acetyl, propionyl and butyryl; aralkanoyl such as phenylacetyl; aroyl such as benzoyl or tolyl; aryloxyalkanoyl such as POA; alkoxycarbonyl such as methoxycarbonyl, ethoxycarbonyl, 2,2,2-trichloroethoxycarbonyl, BOC or 2-iodoethoxycarbonyl; aralkyloxycarbonyl such as CBZ ("carbobenzoxy"), 4-methoxybenzyloxycarbonyl or FMOC; arylsulphonyl such as Mtr. Those amino-protecting groups which are preferred are BOC and Mtr, and also CBZ, Fmoc, benzyl and acetyl.

The expression "hydroxyl-protecting group" is likewise well known and refers to groups which are suitable for protecting an hydroxyl group from chemical reactions but which can readily be removed after the desired chemical reaction has been carried out at other sites in the molecule. The abovementioned unsubstituted or substituted aryl, aralkyl or acyl groups, and also alkyl groups, are typical groups of this nature. The nature and size of the hydroxyl-protecting groups is not critical since the groups are removed once again after the desired chemical reaction or reaction sequence; groups having 1–20, in particular 1–10, carbon atoms are preferred. Examples of hydroxyl-protecting groups are, inter alia, benzyl, p-nitrobenzoyl, p-toluenesulphonyl, tert-butyl and acetyl, with benzyl and tert-butyl being particularly preferred. The COOH groups in aspartic acid and glutamic acid are preferably protected in the form of their tert-butyl esters (for example Asp(OBut)).

The compounds of the formula I are—depending on the protecting group employed—liberated from their functional derivatives using, for example, strong acids, expediently TFA or perchloric acid, but also other strong inorganic acids, such as hydrochloric acid or sulphuric acid, strong organic carboxylic acids, such as trichloroacetic acid, or sulphonic acids, such as benzenesulphonic acid or p-toluenesulphonic acid. It is possible, but not always necessary, for an additional inert solvent to be present. Suitable inert solvents are preferably organic, for example carboxylic acids such as acetic acid, ethers such as tetrahydrofuran or dioxane, amides such as DMF, halogenated hydrocarbons such as dichloromethane, and also alcohols such as methanol, ethanol or isopropanol, and also water. Mixtures of the previously mentioned solvents are also suitable. TFA is preferably used in excess without adding any other solvent, while perchloric acid is used in the form of a mixture of acetic acid and 70% perchloric acid in a ratio of 9:1. The reaction temperatures for the cleavage are expediently between about 0° and 50°, with the cleavage preferably being carried out at between 15 and 30° or room temperature.

The BOC, OBut and Mtr groups can preferably be eliminated, for example, using TFA in dichloromethane or using approximately 3 to 5 n HCl in dioxane at 15–30°, while the FMOC group can preferably be eliminated using an approximately 5 to 50% solution of dimethylamine, diethylamine or piperidine in DMF at 15–30°.

The trityl group is employed for protecting the amino acids histidine, asparagine, glutamine and cysteine. Depending on the desired end product, it is eliminated using TFA/10% thiophenol, with the trityl group being eliminated from all the said amino acids; when TFA/anisole or TFA/thioanisole is used, the trityl group is only eliminated from His, Asn and Gln, whereas it remains on the Cys side chain.

Hydrogenolytically removable protecting groups (for example CBZ or benzyl) can, for example, be eliminated by treating with hydrogen in the presence of a catalyst (for example a precious metal catalyst such as palladium, expediently on a support such as carbon). Suitable solvents in this context are the abovementioned solvents, in particular, for example, alcohols such as methanol or ethanol or amides such as DMF. As a rule, the hydrogenolysis is carried out at temperatures of between about 0 and 100° and pressures of between 1 and 200 bar, preferably at 20–30° and 1–10 bar. The CBZ group is satisfactorily eliminated hydrogenolytically on 5 to 10% Pd/C in methanol or using ammonium formate (in place of hydrogen) on Pd/C in methanol/DMF at 20–30°.

A base of the formula I can be converted with an acid into the associated acid addition salt, for example by reacting equivalent quantities of the base and the acid in an inert solvent such as ethanol and then concentrating by evaporation. Suitable acids for this reaction are, in particular, those which give rise to physiologically harmless salts. Thus, use can be made of inorganic acids, for example sulphuric acid, nitric acid, hydrohalic acids such as hydrochloric acid or hydrobromic acid, phosphoric acids such as orthophosphoric acid, and sulphamic acid, and, in addition, organic acids, in particular aliphatic, alicyclic, araliphatic, aromatic or heterocyclic monobasic or polybasic carboxylic, sulphonic or sulphuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalenemonosulphonic acid, naphthalenedisulphonic acid and lauryl sulphuric acid. Salts with acids which are not physiologically harmless, for example picrates, may be used for isolating and/or purifying the compounds of the formula I.

On the other hand, an acid of the formula I can be converted into one of its physiologically harmless metal or ammonium salts by reaction with a base. In this context, the sodium, potassium, magnesium, calcium and ammonium salts are particularly suitable as salts, as are also substituted ammonium salts, for example the dimethyl-, diethyl- or diisopropylammonium salts, monoethyl-, diethyl- or diisopropylammonium salts, cyclohexyl- and dicyclohexylammonium salts, and dibenzylethylenediammonium salts, and also, for example, salts with arginine or lysine.

The invention furthermore relates to the use of the compounds of the formula I and/or their physiologically harmless salts for producing pharmaceutical preparations, in particular by a non-chemical route. In this context, they can be brought into a suitable dosage form together with at least one solid, liquid and/or semisolid carrier substance or auxiliary substance and, where appropriate, in combination with one or more additional active compounds.

The invention furthermore relates to pharmaceutical preparations which contain at least one compound of the formula I and/or one of its physiologically harmless salts.

These preparations may be used as pharmaceuticals in human and veterinary medicine. Suitable carrier substances are organic or inorganic substances which are suitable for enteral (for example oral), parenteral or topical administration or for administration in the form of an inhalation spray and which do not react with the novel compounds, for example water, vegetable oils, benzyl alcohols, alkylene glycols, polyethylene glycols, glycerol triacetate, gelatin, carbohydrates such as lactose or starch, magnesium stearate, talc or vaseline. For oral employment, use is made, in particular, of tablets, pills, coated tablets, capsules, powders, granules, syrups, juices or drops, for rectal employment of suppositories, for parenteral employment of solutions, preferably oily or aqueous solutions, and also suspensions, emulsions or implants, and, for topical employment, of ointment, creams or powders. The novel compounds can also be lyophilized and the resulting lyophilizates used, for example, for producing injection preparations. The preparations mentioned can be sterilized and/or contain auxiliary substances such as lubricants, preservatives, stabilizers, wetting agents, emulsifiers, salts for influencing the osmotic pressure, buffering substances, dyes, flavourings and/or several additional active compounds, for example one or more vitamins. For administration as an inhalation spray, sprays can be used which contain the active compound either dissolved or suspended in a propellant gas or propellant gas mixture (for example $CO_2$ or fluorochlorohydrocarbons). In this context, the active compound is expediently used in micronized form, with it being possible for one or more additional physiologically tolerated solvents, for example ethanol, to be present. Inhalation solutions can be administered using customary inhalers.

The compounds of the formula I and their physiologically harmless salts may be used as integrin inhibitors in the control of diseases, in particular pathologically angiogenic diseases, thromboses, cardiac infarct, coronary heart diseases, arteriosclerosis, tumours, osteoporosis, inflammations and infections.

In this connection, the substances according to the invention can, as a rule, be administered in analogy with other known, commercially available peptides, in particular, however, in analogy with the compounds described in U.S. Pat. No. 4,472,305, preferably in dosages of between 0.05 and 500 mg, in particular between 0.5 and 100 mg per dosage unit. The daily dose is preferably between about 0.01 and 2 mg/kg of body weight. However, the special dose for each patient depends on a very wide variety of factors, for example on the activity of the special compound employed, on age, body weight, general state of health, sex, diet, time and route of administration, the excretion rate, pharmaceutical combination and severity of the particular disease to which the therapy applies. Parenteral administration is preferred.

In addition, the novel compounds of the formula I can be used in analytical biology and molecular biology.

The novel compounds of the formula I, in which X is a fluorescent dye residue which is linked by way of a —CONH—, —COO—, —NH—C(=S)—NH—, —NH—C(=O)—NH—, —SO$_2$NH— or —NHCO— bond, can be used as diagnostic markers in FACS (fluorescence activated cell sorter) analysis and fluorescence microscopy.

The use of labelled compounds in fluorescence microscopy is described, for example, by Y.-L. Wang and D. L. Taylor in "Fluorescence Microscopy of Living Cells in Culture, Part A+B, Academic Press, Inc. 1989".

The novel compounds of the formula I may also be used in affinity chromatography for eluting bound proteins.

In particular, they may be used as integrin ligands for eluting integrins.

Both in the above text and in that which follows all temperatures are given in ° C. In the following examples, "customary working-up" denotes: water is added, if required, the pH is adjusted, if required and depending on the constitution of the end product, to values of between 2 and 10, the mixture is extracted with ethyl acetate or dichloromethane, the phases are separated, the organic phase is dried over sodium sulphate and evaporated, and the residue is purified by chromatography on silica gel and/or by crystallization. Rf values on silica gel; mobile phase: ethyl acetate/methanol 9:1.

RT=retention time (minutes) in HPLC in the following systems:

[A]
  Column: Nucleosil 7C 18 250×4 mm
  Eluent A: 0.1% TFA in water
  Eluent B: 0.1% TFA in acetonitrile
  Flow rate: 1 ml/min
  Gradient: 20–50% B/30 min.

[B]
  50 minute gradient of 0–80% 2-propanol in water containing 0.3% TFA at 1 ml/min on a Lichrosorb® RP Select B (7 μm) 250×4 mm column

[C]
  Column: Lichrospher (5 μm) 100 RP8 125×4 mm
  Eluent A: 0.1 M Na phosphate pH 7.0
  Eluent B: 0.005 M Na phosphate, pH 7.0/60 vol % of 2-propanol
  Flow rate: 0.7 ml/min
  Gradient: 1–99% B/50 min.
  Mass spectrometry (MS): EI(electron collision ionization) M$^+$; FAB (fast atom bombardment) (M+H)$^+$.

EXAMPLE 1

1.0 g of 0-acetyl salicylic acid N-succinimidyl ester [obtainable by reacting acetylsalicylic acid with HONSu in ethyl acetate, DMF and 1.2 equivalents of diisopropylcarbodiimide, FAB 278] and 0.5 g of triethylamine are added to a solution of 3.05 g of cyclo-(Arg-Gly-Asp-D-Phe-Lys)(SEQ ID NO: 176) [obtainable by cyclizing H-Arg(Mtr)-Gly-Asp(OBut)-D-Phe-Lys(BOC)—OH(SEQ ID NO: 177) to give cyclo-(Arg(Mtr)-Gly-Asp(OBut)-D-Phe-Lys(BOC))(SEQ ID NO: 177) and then eliminating the protecting groups] in 100 ml of DMF. The mixture is stirred at room temperature for 5 hours and cyclo-(Arg-Gly-Asp-D-Phe-Lys(N$^\epsilon$-Sal))(SEQ ID NO: 1)×TFA; RT[B] 22.0; FAB 724 is obtained after the customary working-up and with the concomitant elimination of the acetyl group.

The following are obtained in an analogous manner by reacting cyclo-(Arg-Gly-Asp-D-Phe-Lys)(SEQ ID NO: 176) with phenylpropionic acid N-succinimidyl ester (PhEtCO-ONSu):
  cyclo-(Arg-Gly-Asp-D-Phe-Lys(N$^\epsilon$-PhEtCo))(SEQ ID NO: 2)×TFA; RT [C] 28.2; FAB 736;
with 3,3,3-tris-(4-chlorophenyl)-propionic acid N-succinimidyl ester (TCPP-ONSu):
  cyclo-(Arg-Gly-AspD-Phe-Lys(N$^\epsilon$-TCPP)(SEQ ID NO: 3)×TFA; RT [B] 33.19; FAB 992;
with S-tritylmercaptopropionic acid N-succinimidyl ester (TrtSEtCO-ONSu):
  cyclo-(Arg-Gly-Asp-D-Phe)Lys(N$^\epsilon$TrtSEtCO))(SEQ ID NO: 4)×TFA; RT [B] 33.4; FAB 934;
with benzyloxycarbonyl chloride (CBZ-Cl):
  cyclo-(Arg-Gly-Asp-D-Phe-Lys(N$^\epsilon$-CBZ))(SEQ ID NO: 5);
with octanoyl anhydride:
  cyclo-(Arg-Gly-Asp-D-Phe-Lys(N$^\epsilon$-Oct)(SEQ ID NO: 6)×TFA; RT [B] 27.58; FAB 730;
with acetic anhydride:
  cyclo-(Arg-Gly-Asp-D-Phe-Lys(N$^\epsilon$-Ac))(SEQ ID NO: 7)×TFA; RT [B] 17.02; FAB 646;
with FCA-N-succinimidyl ester:
  cyclo-((Arg-Gly-Asp-D-Phe-Lys(N$^\epsilon$-FCA))(SEQ ID NO: 8) RT [B] 24.18; FAB 962;
with FITC:
  cyclo-(Arg-Gly-Asp-D-Phe-Lys(N$^\epsilon$-FTH))(SEQ ID NO: 9)×TFA; RT [B] 27.3; FAB 994, from which the internal salt can be obtained using NH4HCO3, RT [B] 22.26;

The following are obtained in an analogous manner by reacting cyclo-(Arg-Gly-Asp-D-Phe-N-Me-Lys)(SEQ ID NO: 10) with FITC:
  cyclo-(Arg-Gly-Asp-D-Phe-N(Me)-Lys(N$^\epsilon$-FTH))(SEQ ID NO: 11); RT [B] 22.64; FAB 1007;
with benzyloxycarbonyl chloride (CBZ-Cl):
  cyclo-(Arg-Gly-Asp-D-Phe-N(Me)-Lys(N$^\epsilon$-CBZ))(SEQ ID NO: 12); RT 23.35; FAB 752.

EXAMPLE 2

6 g of BOC-Aha-N-succinimidyl ester are added to a solution of 3.05 g of cyclo-(Arg-Gly-Asp-D-Phe-Lys)(SEQ ID NO: 176) in 40 ml of 5% aqueous NaHCO$_3$ and 40 ml of THF. The mixture is stirred for 4 hours and worked-up in the customary manner, affording cyclo-(Arg-Gly-Asp-D-Phe-Lys (BOC-Aha))(SEQ ID NO: 13); RT [C] 27.7; FAB 817. After the BOC group has been eliminated in HCl/dioxane, cyclo-(Arg-Gly-Asp-D-Phe-Lys(N$^\epsilon$-Aha)(SEQ ID NO: 14)×2 TFA; RT [C] 14.76; FAB 717 is obtained after the customary working-up. Cyclo-(Arg-Gly-Asp-D-Phe-Lys (N$^\epsilon$-FCA-Aha))(SEQ ID NO: 15)×TFA; RT [B] 23.8; FAB 1075 is obtained, in analogy with Example 1, by subsequent reaction with FCA-N-succinimidyl ester.

The following are obtained in an analogous manner by reacting cyclo-(Arg-Gly-Asp-D-Phe-Lys(N$^\epsilon$-Aha)(SEQ ID NO: 14)
with FITC:
    cyclo-(Arg-Gly-Asp-D-Phe-Lys(SEQ ID NO: 16)(N$^\epsilon$-FTH-Aha))
with acetic anhydride:
    cyclo-(Arg-Gly-Asp-D-Phe-Lys(SEQ ID NO: 17)(N$^\epsilon$-Ac-Aha))×TFA; RT [B] 17.1; FAB 759;

EXAMPLE 3

In analogy with Example 2, cyclo-(Arg-Gly-Asp-D-Phe-Lys(N$^\epsilon$-BOC-Aha)-Gly)(SEQ ID NO: 18) is obtained from cyclo-(Arg-Gly-Asp-D-Phe-Lys-Gly)(SEQ ID NO: 178) [obtainable by cyclizing H-Arg(Mtr)-Gly-Asp(OBut)-D-Phe-Lys(BOC)-Gly-OH(SEQ ID NO: 179) to give cyclo-(Arg(Mtr)-Gly-Asp(OBut)-D-Phe-Lys(BOC)-Gly)(SEQ ID NO: 179) and then eliminating the protecting groups] and BOC-Aha-N-succinimidyl ester;

After eliminating the BOC group in HCl/dioxane, cyclo-(Arg-Gly-Asp-D-Phe-Lys(N$^\epsilon$-Aha)-Gly)(SEQ ID NO: 19)×2 TFA is obtained after the customary working-up.

The following is obtained, in analogy with Example 1, by subsequently reacting cyclo-(Arg-Gly-Asp-D-Phe-Lys(N$^\epsilon$-Aha)-Gly(SEQ ID NO: 19)×2 TFA with phenylpropionic acid N-succinimidyl ester:
    Cyclo-(Arg-Gly-Asp-D-Phe-Lys(N$^\epsilon$-PhEtCO-Aha)-Gly) (SEQ ID NO: 20).

The following are obtained in an analogous manner by reacting cyclo-(Arg-Gly-Asp-D-Phe-Lys(N$^\epsilon$-Aha)-Gly) (SEQ ID NO: 19)
with octanoyl anhydride:
    Cyclo-(Arg-Gly-Asp-D-Phe-Lys(N$^\epsilon$-Oct-Aha)-Gly)(SEQ ID NO: 21)
with FCA-N-succinimidyl ester:
    Cyclo-(Arg-Gly-Asp-D-Phe-Lys(N$^\epsilon$-FCA-Aha)-Gly) (SEQ ID NO: 22)
with FITC:
    Cyclo-(Arg-Gly-Asp-D-Phe-Lys(N$^\epsilon$-FTH-Aha)-Gly) (SEQ ID NO: 23).

In analogy with Example 2, cyclo-(Arg-Gly-Asp-D-Phe-Val-Lys-(N$^\epsilon$-BOC-Aha)) (SEQ ID NO: 24)×TFA is obtained from cyclo-(Arg-Gly-Asp-D-Phe-Val-Lys)(SEQ ID NO: 180) [obtainable by cyclizing H-Arg(Mtr)-Gly-Asp(OBut)-D-Phe-Val-Lys(BOC)-OH to give cyclo-(Arg(Mtr)-Gly-Asp (OBut)-D-Phe-Val-Lys(BOC))(SEQ ID NO: 181), and then eliminating the protecting groups] and BOC-Aha-N-succinimidyl ester.

After the BOC group is eliminated in HCl/dioxane, cyclo-(Arg-Gly-Asp-D-Phe-Val-Lys(N$^\epsilon$-Aha)(SEQ ID NO: 25)×2 TFA is obtained after the customary working-up.

In analogy with Example 1, cyclo-(Arg-Gly-Asp-D-Phe-Val-Lys(N$^\epsilon$-PhEtCo-Aha)) (SEQ ID NO: 26) is obtained by subsequently reacting cyclo-(Arg-Gly-Asp-D-Phe-Val-Lys (N$^\epsilon$-Aha))(SEQ ID NO: 25)×2 TFA with phenylpropionic acid N-succinimidyl ester.

EXAMPLE 4

In analogy with Example 2, reaction of BOC-aminocaproic acid N-succinimidyl ester with the following cyclic compounds Cyclo-(Arg-Gly-Asp-D-Trp-Lys)(SEQ ID NO: 182)
    Cyclo-(Arg-Gly-Asp-D-Tyr-Lys)(SEQ ID NO: 183)
    Cyclo-(Arg-Gly-Asp-D-Phe-D-Lys)(SEQ ID NO: 184)
    Cyclo-(Arg-Gly-Asp-D-Phe-Cys)(SEQ ID NO: 185)
    Cyclo Arg-Gly-Asp-D-Phe-Dab)(SEQ ID NO: 186)
    Cyclo-(Arg-Gly-Asp-D-Trp-D-Cys)(SEQ ID NO: 187)
    Cyclo-(Arg-Gly-Asp-D-Tyr-D-Cys)(SEQ ID NO: 188)
    Cyclo-(Arg-Gly-Asp-Phe-D-Lys)(SEQ ID NO: 189)
    Cyclo-(Arg-Gly-Asp-Trp-D-Lys)(SEQ ID NO: 190)
    Cyclo-(Arg-Gly-Asp-Tyr-D-Lys)(SEQ ID NO: 191)
    Cyclo-(Arg-Gly-Asp-Phe-D-Cys)(SEQ ID NO: 192)
    Cyclo-(Arg-Gly-Asp-Phe-Dab)(SEQ ID NO: 193)
    Cyclo-(Arg-Gly-Asp-Trp-D-Cys)(SEQ ID NO: 194)
    Cyclo-(Arg-Gly-Asp-Tyr-D-Cys)(SEQ ID NO: 195)
    Cyclo-(Arg-Gly-Asp-D-Trp-Orn)(SEQ ID NO: 196)
    Cyclo-(Arg-Gly-Asp-D-Tyr-Orn)(SEQ ID NO: 197)
    Cyclo-(Arg-Gly-Asp-D-Phe-Orn)(SEQ ID NO: 198)
    Cyclo-(Arg-Gly-Asp-D-Trp-Orn)(SEQ ID NO: 199)
    Cyclo-(Arg-Gly-Asp-D-Tyr-D-Orn)(SEQ ID NO: 200)
    Cyclo-(Arg-Gly-Asp-D-Phe-D-Orn)(SEQ ID NO: 201)
    Cyclo-(Arg-Gly-Asp-D-Trp-Dab)(SEQ ID NO: 202)
    Cyclo-(Arg-Gly-Asp-D-Tyr-Dab)(SEQ ID NO: 203)
    Cyclo-(Arg-Gly-Asp-D-Tyr-Dap)(SEQ ID NO: 204)
    Cyclo-(Arg-Gly-Asp-D-Tyr-Dap)(SEQ ID NO: 205)
    Cyclo-(Arg-Gly-Asp-D-Phe-Dap)(SEQ ID NO: 206)
    Cyclo-(Arg-Gly-Asp-D-Tyr-D-Dap)(SEQ ID NO: 207)
    Cyclo-(Arg-Gly-Asp-D-Tyr-D-Dap)(SEQ ID NO: 208)
    Cyclo-(Arg-Gly-Asp-D-Phe-D-Dap)(SEQ ID NO: 209)
gives the following peptides:
    Cyclo-(Arg-Gly-Asp-D-Trp-Lys(N$^\epsilon$-BOC-Aha))(SEQ ID NO: 27)
    Cyclo-(Arg-Gly-Asp-D-Trp-Lys(N$^\epsilon$-BOC-Aha))(SEQ ID NO: 28)
    Cyclo-(Arg-Gly-Asp-D-Phe-DLy(N$^\epsilon$-BOC-Aha))(SEQ ID NO: 29)
    Cyclo-(Arg-Gly-Asp-D-Phe-Cys(S-BOC-Aha))(SEQ ID NO: 30)
    Cyclo-(Arg-Gly-Asp-D-Phe-Dab(N$^\gamma$-BOC-Aha))(SEQ ID NO: 31)
    Cyclo-(Arg-Gly-Asp-D-Tyr-D-Cys(S-BOC-Aha))(SEQ ID NO: 32)
    Cyclo-(Arg-Gly-Asp-D-Tyr-D-Cys(S-BOC-Aha))(SEQ ID NO: 33)
    Cyclo-(Arg-Gly-Asp-Phe-p-Lys(N$^\epsilon$-BOC-Aha))(SEQ ID NO: 34)
    Cyclo-(Arg-Gly-Asp-Trp-D-Lys(N$^\epsilon$-BOC-Aha))(SEQ ID NO: 35)
    Cyclo-(Arg-Gly-Asp-Tyr-D-Lys(N$^\epsilon$-BOC-Aha))(SEQ ID NO: 36)

Cyclo-(Arg-Gly-Asp-Phe-D-Cys(S-BOC-Aha))(SEQ ID NO: 37)
Cyclo-(Arg-Gly-Asp-Phe-Dab(N$^\gamma$-BOC-Aha))(SEQ ID NO: 38)
Cyclo-(Arg-Gly-Asp-Trp-D-Cys(S-BOC-Aha))(SEQ ID NO: 39)
Cyclo-(Arg-Gly-Asp-Tyr-D-Cys(S-BOC-Aha))(SEQ ID NO: 40)
Cyclo-(Arg-Gly-Asp-D-Trp-Orn(N$^\delta$-BOC-Aha))(SEQ ID NO: 41)
Cyclo-(Arg-Gly-Asp-D-Tyr-Orn(N$^\delta$-BOC-Aha))(SEQ ID NO: 42)
Cyclo-(Arg-Gly-Asp-D-Phe-Orn(N$^\delta$-BOC-Aha))(SEQ ID NO: 43)
Cyclo-(Arg-Gly-Asp-D-Trp-D-Orn(N$^\delta$-BOC-Aha))(SEQ ID NO: 44)
Cyclo-(Arg-Gly-Asp-D-Tyr-D-Orn(N$^\delta$-BOC-Aha))(SEQ ID NO: 45)
Cyclo-(Arg-Gly-Asp-D-Phe-D-Orn(N$^\delta$-BOC-Aha))(SEQ ID NO: 46)
Cyclo-(Arg-Gly-Asp-D-Trp-Dab(N$^\gamma$-BOC-Aha))(SEQ ID NO: 47)
Cyclo-(Arg-Gly-Asp-D-Tyr-Dab(N$^\gamma$-BOC-Aha))(SEQ ID NO: 48)
Cyclo-(Arg-Gly-Asp-D-Trp-Dap(N$^\beta$-BOC-Aha))(SEQ ID NO: 49)
Cyclo-(Arg-Gly-Asp-D-Tyr-Dap(N$^\beta$-BOC-Aha))(SEQ ID NO: 50)
Cyclo-(Arg-Gly-Asp-D-Phe-Dap(N$^\beta$-BOC-Aha))(SEQ ID NO: 51)
Cyclo-(Arg-Gly-Asp-D-Trp-D-Dap(N$^\beta$-BOC-Aha))(SEQ ID NO: 52)
Cyclo-(Arg-Gly-Asp-D-Tyr-D-Dap(N$^\beta$-BOC-Aha))(SEQ ID NO: 53)
Cyclo-(Arg-Gly-Asp-D-Phe-D-Dap(N$^\beta$-BOC-Aha)), (SEQ ID NO: 54).

After eliminating the BOC group in HCl/dioxane, the following compounds ("A") are obtained:

Cyclo-(Arg-Gly-Asp-D-Trp-Lys(N$^\epsilon$-Aha))(SEQ ID NO: 55)
Cyclo-(Arg-Gly-Asp-D-Tyr-Lys(N$^\epsilon$-Aha))(SEQ ID NO: 56)
Cyclo-(Arg-Gly-Asp-D-Phe-D-Lys(N$^\epsilon$-Aha))(SEQ ID NO: 57)
Cyclo-(Arg-Gly-Asp-D-Phe-Cys(S-Aha))(SEQ ID NO: 58)
Cyclo-(Arg-Gly-Asp-D-Phe-Dab(N$^\gamma$-Aha))(SEQ ID NO: 59)
Cyclo-(Arg-Gly-Asp-D-Trp-D-Cys(S-Aha))(SEQ ID NO: 60)
Cyclo-(Arg-Gly-Asp-D-Tyr-D-Cys(S-Aha))(SEQ ID NO: 61)
Cyclo-(Arg-Gly-Asp-Phe-D-Lys(N$^\epsilon$-Aha))(SEQ ID NO: 62)
Cyclo-(Arg-Gly-Asp-Typ-D-Lys(N$^\epsilon$-Aha))(SEQ ID NO: 63)
Cyclo-(Arg-Gly-Asp-Typ-D-Lys(N$^\epsilon$-Aha))(SEQ ID NO: 64)
Cyclo-(Arg-Gly-Asp-Phe-D-Cys(S-Aha))(SEQ ID NO: 65)
Cyclo-(Arg-Gly-Asp-Phe-Dab(N$^\gamma$-Aha))(SEQ ID NO: 66)
Cyclo-(Arg-Gly-Asp-Trp-D-Cys(S-Aha))(SEQ ID NO: 67)
Cyclo-(Arg-Gly-Asp-Tyr-D-Cys(S-Aha))(SEQ ID NO: 68)
Cyclo-(Arg-Gly-Asp-D-Trp-Orn(N$^\delta$-Aha))(SEQ ID NO: 69)
Cyclo-(Arg-Gly-Asp-D-Tyr-Orn(N$^\delta$-Aha))(SEQ ID NO: 70)
Cyclo-(Arg-Gly-Asp-D-Phe-Orn(N$^\delta$-Aha))(SEQ ID NO: 71)
Cyclo-(Arg-Gly-Asp-D-Trp-D-Orn(N$^\delta$-Aha))(SEQ ID NO: 72)
Cyclo-(Arg-Gly-Asp-D-Tyr-D-Orn(N$^\delta$-Aha))(SEQ ID NO: 73)
Cyclo-(Arg-Gly-AspD-Phe-D-Orn(N$^\delta$-Aha))(SEQ ID NO: 74)
Cyclo-(Arg-Gly-Asp-D-Trp-Dab(N$^\gamma$-Aha))(SEQ ID NO: 75)
Cyclo-(Arg-Gly-Asp-D-Tyr-Dab(N$^\gamma$-Aha))(SEQ ID NO: 76)
Cyclo-(Arg-Gly-Asp-D-Trp-Dap(N$^\beta$-Aha))(SEQ ID NO: 77)
Cyclo-(Arg-Gly-Asp-D-Tyr-Dap(N$^\beta$-Aha))(SEQ ID NO: 78)
Cyclo-(Arg-Gly-Asp-D-Phe-Dap(N$^\beta$-Aha))(SEQ ID NO: 79)
Cyclo-(Arg-Gly-Asp-D-Trp-D-Dap(N$^\beta$-Aha))(SEQ ID NO: 80)
Cyclo-(Arg-Gly-Asp-D-Tyr-D-Dap(N$^\beta$-Aha))(SEQ ID NO: 81)
Cyclo-(Arg-Gly-Asp-D-Phe-D-Dap(N$^\beta$-Aha)), (SEQ ID NO: 82).

The following are obtained by reaction with octanoyl anhydride:

Cyclo-(Arg-Gly-Asp-D-Trp-Lys(N$^\epsilon$-Oct-Aha))(SEQ ID NO: 83)
Cyclo-(Arg-Gly-Asp-D-Tyr-Lys(N$^\epsilon$-Oct-Aha))(SEQ ID NO: 84)
Cyclo-(Arg-Gly-Asp-D-Phe-D-Lys(N$^\epsilon$-Oct-Aha))(SEQ ID NO: 85)
Cyclo-(Arg-Gly-Asp-D-Phe-Cys(S-Oct-Aha))(SEQ ID NO: 86)
Cyclo-(Arg-Gly-Asp-D-Phe-Dab(N$^\gamma$-Oct-Aha))(SEQ ID NO: 87)
Cyclo-(Arg-Gly-Asp-D-Trp-D-Cys(S-Oct-Aha))(SEQ ID NO: 88)
Cyclo-(Arg-Gly-Asp-D-Tyr-D-Cys(S-Oct-Aha))(SEQ ID NO: 89)
Cyclo-(Arg-Gly-Asp-Phe-D-Lys(N$^\epsilon$-Oct-Aha))(SEQ ID NO: 90)
Cyclo-(Arg-Gly-Asp-Trp-D-Lys(N$^\epsilon$-Oct-Aha))(SEQ ID NO: 91)
Cyclo-(Arg-Gly-Asp-Tyr-D-Lys(N$^\epsilon$-Oct-Aha))(SEQ ID NO: 92)
Cyclo-(Arg-Gly-Asp-Phe-D-Cys(S-Oct-Aha))(SEQ ID NO: 93)
Cyclo-(Arg-Gly-Asp-Phe-Dab(N$^\gamma$-Aha))(SEQ ID NO: 94)
Cyclo-(Arg-Gly-Asp-Trp-D-Cys(S-Oct-Aha))(SEQ ID NO: 95)
Cyclo-(Arg-Gly-Asp-Tyr-D-Cys(S-Oct-Aha))(SEQ ID NO: 96)

Cyclo-(Arg-Gly-Asp-D-Trp-Orn(N$^\delta$-Oct-Aha))(SEQ ID NO: 97)
Cyclo-(Arg-Gly-Asp-D-Tyr-Orn(N$^\delta$-Oct-Aha))(SEQ ID NO: 98)
Cyclo-(Arg-Gly-Asp-D-Phe-Orn(N$^\delta$-Oct-Aha))(SEQ ID NO: 99)
Cyclo-(Arg-Gly-Asp-D-TrpD-Orn(N$^\delta$-Oct-Aha))(SEQ ID NO: 100)
Cyclo-(Arg-Gly-Asp-D-Tyr-D-Orn(N$^\delta$-Oct-Aha))(SEQ ID NO: 101)
Cyclo-(Arg-Gly-Asp-D-Phe-D-Orn(N$^\delta$Oct-Aha))(SEQ ID NO: 102)
Cyclo-(Arg-Gly-Asp-D-Trp-Dab(N$^\gamma$-Oct-Aha))(SEQ ID NO: 103)
Cyclo-(Arg-Gly-Asp-D-Trp-Dap(N$^\gamma$-Oct-Aha))(SEQ ID NO: 104)
Cyclo-(Arg-Gly-Asp-D-Trp-Dap(N$^\beta$-Oct-Aha))(SEQ ID NO: 105)
Cyclo-(Arg-Gly-AspD-Tyr-Dap(N$^\beta$-Oct-Aha))(SEQ ID NO: 106)
Cyclo-(Arg-Gly-Asp-D-Phe-Dap(N$^\beta$-Oct-Aha))(SEQ ID NO: 107)
Cyclo-(Arg-Gly-Asp-D-Trp-D-Dap(N$^\beta$-Oct-Aha))(SEQ ID NO: 108)
Cyclo-(Arg-Gly-Asp-D-Tyr-D-Dap(N$^\beta$-Oct-Aha))(SEQ ID NO: 109)
Cyclo-(Arg-Gly-Asp-D-Phe-D-Dap(N$^\beta$-Oct-Aha)), (SEQ ID NO: 110).

The following are obtained by analogous reaction of the "A" compounds with FCA-N-succinimidyl ester:
Cyclo-(Arg-Gly-Asp-D-Trp-Lys(N$^\epsilon$-FCA-Aha))(SEQ ID NO: 111)
Cyclo-(Arg-Gly-Asp-D-Tyr-Lys(N$^\epsilon$-FCA-Aha))(SEQ ID NO: 112)
Cyclo-(Arg-Gly-Asp-D-Phe-D-Lys(N$^\epsilon$-FCA-Aha))(SEQ ID NO: 113)
Cyclo-(Arg-Gly-Asp-D-Phe-Cys(S-FCA-Aha))(SEQ ID NO: 114)
Cyclo-(Arg-Gly-Asp-D-Phe-Dab(N$^\gamma$-FCA-Aha))(SEQ ID NO: 115)
Cyclo-(Arg-Gly-Asp-D-Trp-D-Cys(S-FCA-Aha))(SEQ ID NO: 116)
Cyclo-(Arg-Gly-Asp-D-Tyr-D-Cys(S-FCA-Aha))(SEQ ID NO: 117)
Cyclo-(Arg-Gly-Asp-Phe-D-Lys(N$^\epsilon$-FCA-Aha))(SEQ ID NO: 118)
Cyclo-(Arg-Gly-Asp-Trp-D-Lys(N$^\epsilon$-FCA-Aha))(SEQ ID NO: 119)
Cyclo-(Arg-Gly-Asp-Tyr-D-Lys(N$^\epsilon$-FCA-Aha))(SEQ ID NO: 120)
Cyclo-(Arg-Gly-Asp-Phe-D-Cys(S-FCA-Aha))(SEQ ID NO: 121)
Cyclo-(Arg-Gly-Asp-Phe-Dab(N$^\gamma$-FCA-Aha))(SEQ ID NO: 122)
Cyclo-(Arg-Gly-Asp-Trp-D-Cys(S-FCA-Aha))(SEQ ID NO: 123)
Cyclo-(Arg-Gly-Asp-Tyr-D-Cys(S-FCA-Aha))(SEQ ID NO: 124)
Cyclo-(Arg-Gly-Asp-D-Trp-Orn(N$^\delta$-FCA-Aha))(SEQ ID NO: 125)
Cyclo-(Arg-Gly-Asp-D-Tyr-Orn(N$^\delta$-FCA-Aha))(SEQ ID NO: 126)
Cyclo-(Arg-Gly-Asp-D-Phe-Orn(N$^\delta$-FCA-Aha))(SEQ ID NO: 127)
Cyco-(Arg-Gly-Asp-D-Trp-D-Orn(N$^\delta$-FCA-Aha))(SEQ ID NO: 128)
Cyclo-(Arg-Gly-Asp-D-Tyr-D-Orn(N$^\delta$-FCA-Aha))(SEQ ID NO: 129)
Cyclo-(Arg-Gly-Asp-D-Phe-D-Orn(N$^\delta$-FCA-Aha))(SEQ ID NO: 130)
Cyclo-(Arg-Gly-Asp-D-Trp-Dab(N$^\gamma$-FCA-Aha))(SEQ ID NO: 131)
Cyclo-(Arg-Gly-Asp-D-Tyr-Dab(N$^\gamma$-FCA-Aha))(SEQ ID NO: 132)
Cyclo-(Arg-Gly-Asp-D-Trp-Dap(N$^\beta$-FCA-Aha))(SEQ ID NO: 133)
Cyclo-(Arg-Gly-Asp-D-Tyr-Dap(N$^\beta$-FCA-Aha))(SEQ ID NO: 134)
Cyclo-(Arg-Gly-Asp-D-Phe-Dap(N$^\beta$-FCA-Aha))(SEQ ID NO: 135)
Cyclo-(Arg-Gly-Asp-D-Trp-D-Dap(N$^\beta$-FCA-Aha))(SEQ ID NO: 136)
Cyclo-(Arg-Gly-Asp-D-Tyr-D-Dap(N$^\beta$-FCA-Aha))(SEQ ID NO: 137)
Cyclo-(Arg-Gly-Asp-D-Phe-D-Dap(N$^\beta$-FCA-Aha)), (SEQ ID NO: 138).

The following are obtained by analogous reaction of "A" compounds with O-acetylsalicylic acid N-succinimidyl ester:
Cyclo-(Arg-Gly-Asp-D-Trp-Lys(N$^\epsilon$-Ac-Sal-Aha))(SEQ ID NO: 139)
Cyclo-(Arg-Gly-Asp-D-Tyr-Lys(N$^\epsilon$-Ac-Sal-Aha))(SEQ ID NO: 140)
Cyclo-(Arg-Gly-Asp-D-Phe-D-Lys(N$^\epsilon$-Ac-Sal-Aha)) (SEQ ID NO: 141)
Cyclo-(Arg-Gly-Asp-D-Phe-Cys(S-Ac-Sal-Aha))(SEQ ID NO: 142)
Cyclo-(Arg-Gly-Asp-D-Phe-Dab(N$^\gamma$-Ac-Sal-Aha))(SEQ ID NO: 143)
Cyclo-(Arg-Gly-Asp-D-Trp-D-Cys(S-Ac-Sal-Aha))(SEQ ID NO: 144)
Cyclo-(Arg-Gly-Asp-D-Tyr-D-Cys(S-Ac-Sal-Aha))(SEQ ID NO: 145)
Cyclo-(Arg-Gly-Asp-Phe-D-Lys(N$^\epsilon$-Ac-Sal-Aha))(SEQ ID NO: 146)
Cyclo-(Arg-Gly-Asp-Trp-D-Lys(N$^\epsilon$-Ac-Sal-Aha))(SEQ ID NO: 147)
Cyclo-(Arg-Gly-Asp-Tyr-D-Lys(N$^\epsilon$-Ac-Sal-Aha))(SEQ ID NO: 148)
Cyclo-(Arg-Gly-Asp-Phe-D-Cys(S-Ac-Sal-Aha))(SEQ ID NO: 149)
Cyclo-(Arg-Gly-Asp-Phe-Dab(N$^\gamma$-Ac-Sal-Aha))(SEQ ID NO: 150)
Cyclo-(Arg-Gly-Asp-Trp-D-Cys(S-Ac-Sal-Aha))(SEQ ID NO: 151)
Cyclo-(Arg-Gly-Asp-Tyr-D-Cys(S-Ac-Sal-Aha))(SEQ ID NO: 152)
Cyclo-(Arg-Gly-Asp-D-Trp-Orn(N$^\delta$-Ac-Sal-Aha))(SEQ ID NO: 153)
Cyclo-(Arg-Gly-Asp-D-Tyr-Orn(N$^\delta$-Ac-Sal-Aha))(SEQ ID NO: 154)
Cyclo-(Arg-Gly-Asp-D-Phe-Orn(N$^\delta$-Ac-Sal-Aha))(SEQ ID NO: 155)
Cyclo-(Arg-Gly-Asp-D-Trp-D-Orn(N$^\delta$-Ac-Sal-Aha)) (SEQ ID NO: 156)

Cyclo-(Arg-Gly-Asp-D-Tyr-D-Orn(N$^\delta$-Ac-Sal-Aha)) (SEQ ID NO: 157)

Cyclo-(Arg-Gly-Asp-D-Phe-D-Orn(N$^\delta$-Ac-Sal-Aha)) (SEQ ID NO: 158)

Cyclo-(Arg-Gly-Asp-D-Trp-Dab(N$^\gamma$-Ac-Sal-Aha))(SEQ ID NO: 159)

Cyclo-(Arg-Gly-Asp-D-Tyr-Dab(N$^\gamma$-Ac-Sal-Aha))(SEQ ID NO: 160)

Cyclo-(Arg-Gly-Asp-D-Trp-Dap(N$^\beta$-Ac-Sal-Aha))(SEQ ID NO: 161)

Cyclo-(Arg-Gly-Asp-D-Tyr-Dap(N$^\beta$-Ac-Sal-Aha))(SEQ ID NO: 162)

Cyclo-(Arg-Gly-Asp-D-Phe-Dap(N$^\beta$-Ac-Sal-Aha))(SEQ ID NO: 163)

Cyclo-(Arg-Gly-Asp-D-Trp-D-Dap(N$^\beta$-Ac-sal-Aha)) (SEQ ID NO: 164)

Cyclo-(Arg-Gly-Asp-D-Tyr-D-Dap(N$^\beta$-Ac-Sal-Aha)) (SEQ ID NO: 165)

Cyclo-(Arg-Gly-Asp-D-Phe-D-Dap(N$^\beta$-Ac-Sal-Aha)), (SEQ ID NO: 166), with the deacetylated compounds, which are separated off under customary chromatographic conditions, also resulting at the same time.

EXAMPLE 5

Cyclo-(Arg-Gly-Asp-D-Phe-Lys(N$^\epsilon$-HSEtCO))(SEQ ID NO: 167)×TFA; RT [B] 18.54; FAB 692 is obtained, after the customary working-up, by eliminating the trityl group from cyclo-(Arg-Gly-Asp-D-Phe-Lys(SEQ ID NO: 4)(N$^\epsilon$-TrtSEtCO))(SEQ ID NO: 4) using TFA/thiophenol.

EXAMPLE 6

2.0 g of succinic acid N-succinimidyl ester monomethyl ester and 0.5 g of triethylamine are added to a solution of 3.05 g of cyclo-(Arg-Gly-Asp-D-Phe-Lys)(SEQ ID NO: 176) in 100 ml of dichloromethane. The mixture is stirred at room temperature for 5 hours, and cyclo-(Arg-Gly-Asp-D-Phe-Lys (SEQ ID NO: 169) (N$^\epsilon$-H$_3$COCO(CH$_2$)$_2$CO)) (SEQ ID NO: 169) is obtained after the customary working-up. Cyclo-(Arg-Gly-Asp-D-Phe-Lys(N$^\epsilon$-HOCO(CH$_2$)$_2$CO)) (SEQ ID NO: 169) is obtained by hydrolysing the ester with aqueous potassium hydroxide. Cyclo-(Arg-Gly-Asp-D-Phe-Lys(N$^\epsilon$-SuN-O—CO(CH$_2$)$_2$CO)) (SEQ ID NO: 210) is obtained by subsequent reaction with HONSu in ethyl acetate. The following compound is obtained, in analogy with Example 1, by reaction with cyclo-(Arg-Gly-Asp-P-PheLys-Gly)(SEQ ID NO: 178): cyclo-(Arg-Gly-Asp-D-Phe-Lys(N$^\epsilon$—CO(CH$_2$)$_2$CO—R$^2$))(SEQ ID NO: 170), in which R$^2$ is cyclo-(Arg-Gly-Asp-D-Phe-Lys(N$^\epsilon$-)-Gly) (SEQ ID NO: 211).

EXAMPLE 7

0.5 ml of acetic acid and 0.5 g of palladium on active carbon are added to a solution of 1.17 g of cyclo-(Arg(Mtr)-Gly-Asp(OBut)-D-Phe-Lys(CBZ)) in 50 ml of dimethylacetamide, and the mixture is stirred for 2 hours under a hydrogen atmosphere. Cyclo-(Arg(Mtr)Gly-Asp (OBut)-D-Phe-Lys(SEQ ID NO: 212) ("B"); RT [A, 30–80% acetonitrile] 18.6 is obtained after separating off the catalyst and after the customary working-up.

0.075 g of succinic anhydride are added to a solution of 0.3 g of "B" in 15 ml of DMF and the mixture is stirred at room temperature for 12 hours. 0.26 g of cyclo-(Arg(Mtr)-Gly-Asp(OBut)-D-Phe-Lys(N$^\epsilon$—CO—(CH$_2$)$_2$—COOH) (SEQ ID NO: 213) ("C"); RT [A, 30–80% acetonitrile] 19.2; FAB 972 is obtained after the customary working-up.

0.1 g of EDClxHCl, 0.075 g of HOBt and a solution of 0.3 g of "B" in 15 ml of DMF are added to a solution of 0.23 g of "B" in 20 ml of DMF, and the mixture is stirred for 12 hours. Cyclo-(Arg(Mtr)-Gly-Asp(OBut)-D-Phe-Lys)$_2$ (COCH$_2$CH$_2$CO)(SEQ ID NO: 214) ("D"); RT [A, 30–80% acetonitrile] 26.6; FAB 1826 is obtained after the customary working-up.

A solution consisting of 85.5% TFA, 2% water, 2.5% ethanedithiol, 5% phenol, 5% thioanisole and 0.25 g of "D" is stirred at room temperature for 24 hours. Cyclo-(Arg-Gly-Asp-D-Phe-Lys)$_2$(COCH$_2$CH$_2$CO)(SEQ ID NO: 171); RT [A, 10–50% acetonitrile] 20.2; FAB 1289 is obtained after the customary working-up.

The following compound is obtained in an analogous manner from cyclo-(Arg(Mtr)-Gly-Asp(OBut)-D-Phe-Lys (CBZ)(SEQ ID NO: 211) by reacting the latter with dithio-dipropionic acid (DTDP-OH) under the same conditions as previously:

Bis-N$^\epsilon$-cyclo-(Arg-Gly-Asp-D-Phe-Lys)-DTDP(SEQ ID NO: 172); RT 20.73; FAB 1382.

The following examples relate to pharmaceutical preparations:

EXAMPLE A

Injection Vials

A solution of 100 g of an active compound of the formula I and 5 g of disodium hydrogen phosphate is adjusted, in 3 l of double distilled water, to pH 6.5 with 2 n hydrochloric acid, sterilized by filtration and used to fill injection vials; the solution is lyophilized, and the vials sealed, under sterile conditions. Each injection vial contains 5 mg of active compound.

EXAMPLE B

Suppositories

A mixture of 20 g of an active compound of the formula I with 100 g of soya bean lecithin and 1400 g of cocoa butter is melted, poured into moulds and allowed to cool. Each suppository contains 20 mg of active compound.

EXAMPLE C

Solution

A solution is prepared from 1 g of an active compound of the formula I, 9.38 g of NaH$_2$PO$_4$.2H$_2$O, 28.48 g of Na$_2$HPO$_4$.12H$_2$O and 0.1 g of benzalkonium chloride in 940 ml of double distilled water. The solution is adjusted to pH 6.8, made up to 1 l and sterilized by irradiation. This solution can be used in the form of eyedrops.

EXAMPLE D

Ointment 500 mg of an active compound of the formula I is mixed with 99.5 g of vaseline under asceptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed into tablets in a customary manner, such that each tablet contains 10 mg of active compound.

EXAMPLE F

Coated Tablets

Tablets are compressed in analogy with Example E, with the tablets then being coated, in a customary manner, with a coating composed of sucrose, potato starch, talc, tragacanth and dye.

EXAMPLE G

Capsules

Hard gelatine capsules are filled, in a customary manner, with 2 kg of active compound of the formula I such that each capsule contains 20 mg of the active compound.

EXAMPLE H

Ampoules

A solution of 1 kg of active compound of the formula I in 60 l of double distilled water is sterilized by filtration and used to fill ampoules; the solution is lyophilized, and the ampoules are sealed, under sterile conditions. Each ampoule contains 10 mg of active compound.

EXAMPLE I

Inhalation Spray 14 g of active compound of the formula I are dissolved in 10 l of isotonic NaCl solution and the solution is used to fill commercially available spraying vessels which have a pumping mechanism. The solution can be sprayed into the mouth or nose. One spray burst (approximately 0.1 ml) corresponds to a dose of about 0.14 mg.

What is claimed is:

1. A compound of formula I

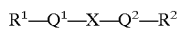     I in which

Q$^1$, Q$^2$ are, in each case independently of each other, either absent or —NH—(CH$_2$)$_n$—CO—, R$^1$, R$^2$ are, in each case independently of each other, either absent or cyclo-(Arg-Gly-Asp-Z), where Z is bonded in the side chain to Q$^1$ or Q$^2$ or, if Q$^1$ and/or Q$^2$ is/are absent, to X, and where at least one of the radicals R$^1$ or R$^2$ must always be present, X is —CO—R$^{18}$—CO—, and if R$^1$—Q$^1$— or R$^2$—Q$^2$— is absent, R$^{10}$, R$^{13}$, R$^{16}$ or a fluorescent dye residue which is linked by way of a —CONH—, —NH—C(=S)—NH— bond, or is salicyloyl, Z is Phe-Lys, where the said amino acids can also be derivatized to N-methyl, N-ethyl, N-propyl, N-benzyl or C$_\alpha$-methyl derivatives and the amino acid residues are linked to each other, in peptide manner, by way of the α-amino and α-carboxyl groups, and R$^{10}$ is alkanoyl having 1–8 carbon atoms which is substituted once by SR$^{11}$, R$^{11}$ is trityl, R$^{13}$ is aroyl having 7–11 carbon atoms which is unsubsituted, R$^{16}$ is aralkanoyl having 7–10 carbon atoms which is unsubstituted, R$^{18}$ is absent, or is R$^{19}$, R$^{19}$ is alkylene having 1–6 carbon atoms, and n is 1, 2, 3, 4 or 5, where, provided that the residues are residues of optically active amino acids and amino acid derivatives, both the D and the L forms are included, and the salts thereof.

2. A compound of formula I according to claim 1

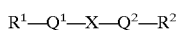

c) in which

Q$^1$, Q$^2$ and R$^2$ are absent,

R$^1$ is cyclo-(Arg-Gly-Asp-D-Phe-Lys)(SEQ ID NO.: 176), and

X is salicyloyl;

d) in which

Q$^1$ and Q$^2$ are absent,

R$^1$ and R$^2$ is cyclo-(Arg-Gly-Asp-D-Phe-Lys)(SEQ ID NO.: 176), and

X is —CO—(CH$_2$)$_2$—CO—;

f) in which

Q$^2$ and R$^2$ are absent,

Q$^1$ is —NH—(CH$_2$)$_5$—CO—

R¹ is cyclo-(Arg-Gly-Asp-D-Phe-Lys)(SEQ ID NO.: 176), and

X is fluoresceinoyl;

and the physiologically harmless salts of the said compounds.

3. A compound of formula I according to claim 1, which is cyclo-(Arg-Gly-Asp-D-Phe-N(Me)-Lys(N$^\epsilon$-FTH)).

4. A compound of formula I according to claim 1, which is cyclo-(Arg-Gly-Asp-D-Phe-Lys(N$^\epsilon$-Sal)), cyclo-(Arg-Gly-Asp-D-Phe-Lys(N$^\epsilon$-PhEtCO)), cyclo-((Arg-Gly-Asp-D-Phe-Lys(N$^\epsilon$-FCA)), cyclo-(Arg-Gly-Asp-D-Phe-Lys(N$^\epsilon$-FTH)), cyclo-(Arg-Gly-Asp-D-Phe-N(Me)-Lys(N$^\epsilon$-CBZ)), cyclo-(Arg-Gly-Asp-D-Phe-Lys(N$^\epsilon$-FTH-Aha)), cyclo-(Arg-Gly-Asp-D-Phe-Lys(N$^\epsilon$-FCA-Aha)-Gly, cyclo-(Arg-Gly-Asp-D-Phe-Lys(N$^\epsilon$-FTH-Aha)-Gly), cyclo-(Arg-Gly-Asp-D-Phe-Lys(N$^\epsilon$-CO(CH$_2$)$_2$CO—R$^2$)), in which R$^2$ is cyclo-(Arg-Gly-Asp-D-Phe-Lys(N$^\epsilon$-)-Gly), cyclo-(Arg-Gly-Asp-D-Phe-Lys)$_2$(COCH$_2$CH$_2$CO), or bis-N$^\epsilon$-cyclo-(Arg-Gly-Asp-D-Phe-Lys)-DtDP.

5. A pharmaceutical composition, comprising at least one compound of formula I according to claim 1 and/or a physiologically harmless salt thereof.

6. A compound of formula I according to claim 1, or a physiologically harmless salt thereof, which is an integrin inhibitor useful for controlling pathologically angiogenic diseases, thrombosis, cardiac infarct, coronary heart diseases, arteriosclerosis, tumors, osteoporosis, inflammations or infections.

7. A process for preparing a compound of formula I according to claim 1, or a salt thereof, comprising a) reacting a compound of formula II

H—Q¹—R¹    II in which

Q¹ and R¹ have the meaning given in claim 1, in an acylation reaction, with a compound of formula III

X—L    III in which

X has the meaning given in claim 1, and

L is Cl, Br, I or a free or reactive functionally modified OH group, or b) reacting a compound of formula IV

H—Q²—R²    IV in which

Q² and R² have the meaning given in claim 1, in an acylation reaction, with a compound of formula V

R¹—Q¹—X—L    V in which

R¹, Q¹, X and L have the given meaning, or c) reacting a compound of formula II

H—Q¹—R¹    II in which

Q¹ and R¹ have the meaning given in claim 1, in an addition reaction, with a compound of formula VI

X—U    VI in which

X has the meaning given in claim 1, and

U is —N=C=O, —N=C=S or maleimidyl, or d) treating a functional derivative thereof with a solvolysing or hydrogenolysing agent, and/or converting a basic or acidic compound of formula I into one of its salts by treating with an acid or base.

8. A process for producing a pharmaceutical composition, comprising bringing together a compound of formula I according to claim 1, and/or one of its physiologically harmless salts, with at least one solid, liquid or semisolid carrier substance or auxiliary substance.

9. A method of FACS analysis or fluorescence microscopy, comprising conducting FACS analysis or fluorescence microscopy with the aid of a diagnostic marker, wherein the marker is a compound of formula I according to claim 1, where X is a fluorescent dye residue which is linked by way of a —CONH— or —NH—C(=S)—NH— bond.

10. A method of FACS analysis or fluorescence microscopy, comprising conducting FACS analysis or fluorescence microscopy with the aid of a diagnostic marker, wherein the marker is a compound of formula I according to claim 1, where X is a fluorescent dye residue which is linked by way of a —CONH— or —NH—C(=S)—NH— bond, or is salicyloyl.

* * * * *